US007879858B2

(12) United States Patent
Merla et al.

(10) Patent No.: US 7,879,858 B2
(45) Date of Patent: *Feb. 1, 2011

(54) SUBSTITUTED TETRAHYDROPYRROLOPYRAZINE COMPOUNDS AND THE USE THEREOF IN PHARMACEUTICAL COMPOSITIONS

(75) Inventors: Beatrix Merla, Aachen (DE); Thomas Christoph, Aachen (DE); Stefan Oberboersch, Aachen (DE); Klaus Schiene, Duesseldorf (DE); Gregor Bahrenberg, Aachen (DE); Robert Frank, Aachen (DE); Sven Kuehnert, Dueren (DE); Wolfgang Schroeder, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/425,873

(22) Filed: Apr. 17, 2009

(65) Prior Publication Data
US 2009/0258880 A1 Oct. 15, 2009

Related U.S. Application Data

(63) Continuation of application No. PCT/EP2007/008956, filed on Oct. 16, 2007.

(30) Foreign Application Priority Data

Oct. 17, 2006 (DE) ........................ 10 2006 049 452

(51) Int. Cl.
A61K 31/495 (2006.01)
(52) U.S. Cl. ................... 514/249; 544/349; 549/59; 549/505
(58) Field of Classification Search ............... 514/249; 544/349; 549/59, 505
See application file for complete search history.

(56) References Cited

U.S. PATENT DOCUMENTS

| 4,188,389 | A | 2/1980 | Jirkovsky |
| 5,292,732 | A | 3/1994 | Roever |
| 2002/0128277 | A1 | 9/2002 | Dworetzky et al. |
| 2005/0054651 | A1 | 3/2005 | Natarajan et al. |

FOREIGN PATENT DOCUMENTS

| CA | 2097465 A1 | 12/1993 |
| EP | 0 521 368 A1 | 1/1993 |
| EP | 0 572 863 A1 | 12/1993 |
| WO | WO 94/29315 A1 | 12/1994 |
| WO | WO 03/024967 A2 | 3/2003 |
| WO | WO 03/084955 A1 | 10/2003 |
| WO | WO 2004/029040 A1 | 4/2004 |
| WO | WO 2004/052864 A1 | 6/2004 |

OTHER PUBLICATIONS

Berman, et al., Biol. Psychiatry, 51(6), 2002, 469-473.*
Li, et al. Org. Lett., 9(20), 2007, 4065-4068.*

Form PCT/IPEA/409 dated Feb. 5, 2009 (Twenty-one pages).
Shirude, P.S., Kumar, V.A., Ganesh, K.N., (2S,5R/2R,5S)-Aminoethylpipecolyl *aepip-aeg*PNA chimera: synthesis and duplex/triplex stability, Tetrahedron 60: 9485-9492 (2004).
Nakao, K. et al., Quantitative Structure-Activity Analyses of Novel Hydroxyphenylurea Derivatives as Antioxidants, *Bioorg. Med. Chem.*, 6:849-868 (1998).
B. L. Bray et al., N-(Triisopropylsilyl)pyrrole, A progenitor "par excellence" of 3-substituted pyrroles, *J. Org. Chem.*, 55(26):6317-6328 (1990).
M. A. Marques et al, Toward an Understanding of the Chemical Etiology for DNA Minor-Broove Recognition by Polyamides, *Helvetica Chimica Acta* 85(12):4485-4517 (2002).
I. Jirkovski und R. Baudy, A Facile, Large-Scale Preparation of 1H-Pyrrole-1-ethanamine and Syntheses of Substituted Pyrrolo[1,2-a]pyrazines and Hydro Derivatives Thereof, *Synthesis*, pp. 481-483, Georg Thieme Verlag, Stuttgart—New York (1981).
I. Castellote et al., Pyrrolodiazines 6, Palladium-Catalyzed Arylation, Heteroarylation, and Amination of 3,4-Dihydropyrrolo[1,2-a]pyrazines, *J. Org. Chem.* 69(25):8668-8675 (2004).
Bennett, Gary J., et al., "A Peripheral Mononeuropathy in Rat That Produces Disorders of Pain Sensation Like Those Seen in Man," Pain, 1988, pp. 87-107, vol. 33, 1988 Elsevier Science Publishers B.V.
Blackburn-Munro, Gordon, et al., "The Anticonvulsant Retigabine Attenuates Nociceptive Behaviors in Rat Models of Persistent and Neuropathic Pain," European Journal of Pharmacology, 2003, pp. 109-116, vol. 460, 2003 Elsevier Science Publishers B.V.
De Sarro, Giovambattista, et al., "Influence of Retigabine on the Anticonvulsant Activity of Some Antiepileptic Drugs Against Audiogenic Seizures in DBA/2 Mice," Naunyn-Schmiedeberg's Arch Pharmacology, 2001, pp. 330-336, vol. 363.
Dost, R., et al., "The Anti-Hyperalgesic Activity of Retigabine is Mediated by KCNQ Potassium Channel Activation," Naunyn-Schmiedeberg's Arch Pharmacology, 2004, pp. 382-390, vol. 369, Springer-Verlag 2004.
Gribkoff, Valentin K., "The Therapeutic Potential of Neuronal KCNQ Channel Modulators," Expert Opinion Ther. Targets, 2003, pp. 737-748, vol. 7, No. 6, Ashley Publications Ltd. 2003.

(Continued)

Primary Examiner—James O Wilson
Assistant Examiner—Douglas M Willis
(74) Attorney, Agent, or Firm—Crowell & Moring LLP

(57) ABSTRACT

Substituted tetrahydropyrrolopyrazine compounds corresponding to formula I

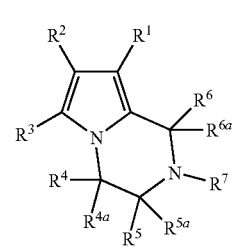

a process for producing such compounds; and a method of using such compounds to treat or inhibit various disorders or disease states including pain, depression and anxiety.

2 Claims, No Drawings

OTHER PUBLICATIONS

Hamill, O.P., et al., "Improved Patch-Clamp Techniques for High-Resolution Current Recording from Cells and Cell-Free Membrane Patches," Pfluegers Archiv European Journal of Physiology, 1981, pp. 85-100, vol. 391, Springer-Verlag 1981.

Kim, Sun Ho, et al., "An Experimental Model for Peripheral Neuropathy Produced by Segmental Spinal Nerve Ligation in the Rat," Pain, 1992, pp. 355-363, vol. 50, 1992 Elsevier Science Publishers B.V.

Korsgaard, M.P.G., et al., "Anxiolytic Effects of Maxipost (BMS-204352) and Retigabine Via Activation of Neuronal $K_v7$ Channels," The Journal of Pharmacology and Experimental Therapeutics, 2005, pp. 282-292, vol. 314, No. 1, 2005 The American Society for Pharmacology and Experimental Therapeutics.

Nielsen, Alexander Norup, et al., "Pharmacological Characterisation of Acid-Induced Muscle Allodynia in Rats," European Journal of Pharmacology, 2004, pp. 93-103, vol. 487, 2004 Elsevier B.V.

Passmore, Gayle M., et al., "KCNQ/M Currents in Sensory Neurons: Significance for Pain Therapy," The Journal of Neuroscience, Aug. 6, 2003, pp. 7227-7236, vol. 23, No. 18, 2003 Society for Neuroscience.

Streng, Tomi, et al., "Urodynamic Effects of the K+ Channel (KCNQ) Opener Retigabine in Freely Moving, Conscious Rats," The Journal of Urology, Nov. 2004, pp. 2054-2058, vol. 172, 2004 American Urological Association.

Wickenden, Alan D., et al., "KCNQ Potassium Channels: Drug Targets for the Treatment of Epilepsy and Pain," Expert Opinion Ther. Patents, 2004, vol. 14, No. 4, 2004 Ashley Publications Ltd.

Jordan, V.C. Nature Reviews: Drug Discovery, 2, 2003, p. 205.

Dorwald, F. Zaragoza. Side Reactions in Organic Synthesis: A Guide to Successful Synthesis Design, Weinheim: Wiley-VCH Verlag GmbH & Co. KGaA, 2005, Preface.

Patani, et al. Chem. Rev., 96, 1996, pp. 3147-3176.

* cited by examiner

SUBSTITUTED TETRAHYDROPYRROLOPYRAZINE COMPOUNDS AND THE USE THEREOF IN PHARMACEUTICAL COMPOSITIONS

CROSS REFERENCE TO RELATED APPLICATIONS

This application is a continuation of international patent application no. PCT/EP2007/008956 filed Oct. 16, 2007 designating the United States of America and published in German on Apr. 24, 2008 as WO 2008/046581, the entire disclosure of which is incorporated herein by reference. Priority is claimed based on Federal Republic of Germany patent application no. DE 10 2006 049 452.0, filed Oct. 17, 2006.

BACKGROUND OF THE INVENTION

The present invention relates to substituted tetrahydropyrrolopyrazine compounds, processes for their preparation, pharmaceutical compositions containing these compounds and the use of these compounds for the preparation of pharmaceutical compositions for the treatment of pain and other conditions.

Treatment of pain, in particular of neuropathic pain, is of great importance in medicine. There is a worldwide need for pain therapies which are effective. The urgent need for action for targeted treatment of chronic and non-chronic states of pain appropriate for the patient, by which is to be understood successful and satisfactory pain treatment for the patient, is also documented in the large number of scientific works which have been published recently in the field of applied analgesics and of basic research into nociception.

Monoamine reuptake inhibitors from the class of tricyclic antidepressants (TCAs) have been successfully employed for treatment of depression since the 1960s. The relevance of dysfunctions of monoaminergic systems with psychiatric diseases is widely acknowledged on the basis of the preclinically and clinically demonstrated antidepressive actions of TCAs, selective serotonin reuptake inhibitors (so-called SSRIs), selective noradrenaline reuptake inhibitors, mixed serotonin and noradrenaline reuptake inhibitors (so-called SNRIs), monoamine oxidase inhibitors and modulators of various serotonin and noradrenaline receptor subtypes (Berman et al., Biol Psychiatry, 2002 Mar. 15; 51(6):469-73). Antidepressants moreover are important adjuvants in pain therapy, in particular for chronic pain. However, an independent analgesic action is induced by monoamine reuptake inhibitors, in that they activate the descending inhibition of spinal nociceptive signals. Good successes are also described in the treatment of urinary incontinence by use of monoamine reuptake inhibitors (Sorbera et al., Drugs of the future, 2000, vol. 25, page 907-916). Monoamine reuptake inhibitors are furthermore suitable for treatment of anxiety states, fibromyalgia, eating disorders, bulimia, hyperactivity (attention deficit hyperactivity disorder; ADHD), drug dependency, addiction and withdrawal, trichotillomania, skin diseases, such as postherpetic neuralgia and pruritus, memory disorders, cognitive disorders and Alzheimer's disease.

Therapeutic use of the antidepressants approved to date is limited by the undesirable side effects which often occur. There may be mentioned here in particular constipation, retention of urine, dryness of the mouth, accommodation disorders, orthostatic hypotension with tachycardia, sedation, serotonin syndrome, sexual dysfunctions, dizziness, cognitive dysfunctions and QT prolongations, incl. torsade de pointes. Disadvantages in the treatment of psychiatric diseases are a late onset of action, a high rate of recurrence and an absence of action in 20-30% of patients.

SUMMARY OF THE INVENTION

It is an object of the present invention to provide new potent monoamine reuptake inhibitors with therapeutically relevant activity components for treating depression, anxiety states and pain. The activities should be at least partly based on inhibition of the reuptake of serotonin (5-HT), noradrenaline (NA) or a combination of these mechanisms.

This and other objects have been achieved by the invention as described and claimed hereinafter.

Surprisingly, it has now been found that substituted tetrahydropyrrolopyrazine compounds corresponding to formula I given below are suitable for treatment of pain and also show a good inhibition of the reuptake of noradrenaline and/or serotonin, and are therefore suitable for treatment of disorders or diseases which are at least partly mediated via the reuptake of noradrenaline and/or serotonin.

Substituted tetrahydropyrrolopyrazines are already known from the literature and from databanks. U.S. Pat. No. 4,188,389 thus discloses tetrahydropyrrolopyrazines which are suitable for treatment of depression. WO 2003024967 discloses tetrahydropyrrolopyrazines which carry a $(C=Z)-NH_2$ substituent on $R^3$ and are suitable for treatment of cancer. Tetrahydropyrrolopyrazines are furthermore listed in databanks, for example at CAS, without information on biological activity being given.

The present invention therefore provides substituted tetrahydropyrrolopyrazine compounds corresponding to formula I

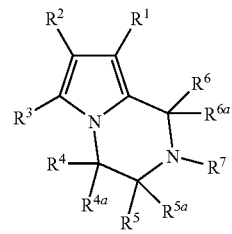

wherein $R^1$, $R^2$ and $R^3$ each independently represent hydrogen, $C_{1-6}$-alkyl, saturated or unsaturated, branched or unbranched, unsubstituted or mono- or polysubstituted; F, Cl, Br, I, CN, $NH_2$, $NH-C_{1-6}$-alkyl, $NH-C_{1-6}$-alkyl-OH, $N(C_{1-6}$-alkyl)$_2$, $N(C_{1-6}$-alkyl-OH)$_2$, NHaryl; NH-alkylaryl; NH-heteroaryl; $NO_2$, SH, $S-C_{1-6}$-alkyl, OH, $O-C_{1-6}$-alkyl, $O-C_{1-6}$-alkyl-OH, $C(=O)C_{1-6}$-alkyl, $NHSO_2C_{1-6}$-alkyl, NHCOaryl; $NHCOC_{1-6}$-alkyl, $CO_2H$, $CH_2SO_2$-phenyl, $CO_2-C_{1-6}$-alkyl, $OCF_3$, $SCF_3$, $CF_3$, benzyloxy, morpholinyl, pyrrolidinyl, piperidinyl, piperazinyl, phenoxy, phenyl, pyridyl, alkylaryl, thienyl or furyl; or $R^1$ and $R^2$ or $R^2$ and $R^3$ form a ring and together denote

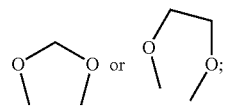

$R^4$ and $R^5$ each independently represent H, F, Cl, Br, I, —CN, $NH_2$, $NH-C_{1-6}$-alkyl, $NH-C_{1-6}$-alkyl-OH, $C_{1-6}$-alkyl, $N(C_{1-6}$-alkyl$)_2$, $N(C_{1-6}$-alkyl-OH$)_2$, $NO_2$, SH, $S-C_{1-6}$-alkyl, S-benzyl, $O-C_{1-6}$-alkyl, OH, $O-C_{1-6}$-alkyl-OH, O-benzyl, $C(=O)C_{1-6}$-alkyl, $CO_2H$, $CO_2-C_{1-6}$-alkyl or benzyl;

$R^6$ represents $C_{1-6}$-alkyl, branched or unbranched, unsubstituted or mono- or polysubstituted; aryl or heteroaryl, unsubstituted or mono- or polysubstituted; or an aryl or heteroaryl radical linked via a $C_{1-3}$-alkyl chain and unsubstituted or mono- or polysubstituted;

$R^{4a}$, $R^{5a}$ and $R^{6a}$ each independently represent H or $C_{1-6}$-alkyl;

$R^7$ represents $C(=O)R^{13}$;

$R^{13}$ denotes $C_{1-6}$-alkyl, saturated or unsaturated, branched or unbranched, unsubstituted or mono- or polysubstituted; aryl, heteroaryl, heterocyclyl or $C_{3-8}$-cycloalkyl, in each case unsubstituted or mono- or polysubstituted; or aryl, heteroaryl, heterocyclyl or $C_{3-8}$-cycloalkyl linked via a $C_{1-5}$-alkyl chain and in each case unsubstituted or mono- or polysubstituted, wherein the alkyl chain can be branched or unbranched, saturated or unsaturated;

with the provisos that if $R^1$-$R^5$ represent H and $R^6$ denotes $C_{1-6}$-alkyl or phenyl, unsubstituted or substituted once to three times by $C_{1-6}$-alkyl or $C_{1-6}$-alkoxy, $R^7$ does not denote $C_{1-5}$-alkyl-phenyl or $C_{1-5}$-alkyl linked via $C(=O)$;

if $R^6$ represents $CH_3$, $R^7$ does not denote $C(=O)CH_2CH_2$-imidazolyl; and if $R^6$ represents phenyl and $R^7$ represents $C(O)R^{13}$, $R^{13}$ does not denote 3-trifluoromethylphenyl, 3,4-dimethoxyphenyl, furanyl, 4-nitrophenyl or 4-methylphenyl; in the form of the racemate; of the enantiomers, diastereomers, mixtures of the enantiomers or diastereomers or of an individual enantiomer or diastereomer; of the bases and/or salts of physiologically acceptable acids.

DETAILED DESCRIPTION OF THE INVENTION

In connection with "phenyl", "phenyloxy", "benzyl", "benzyloxy", "alkylaryl", the term in each case includes the unsubstituted structure and the structure substituted by F, Cl, $OCH_3$, $OCF_3$, $SCF_3$ and $CF_3$ and $CH_3$.

In the context of this invention, the expressions "$C_{1-3}$-alkyl", "$C_{1-5}$-alkyl" and "$C_{1-6}$-alkyl" include acyclic saturated or unsaturated hydrocarbon radicals, which can be branched- or straight-chain and unsubstituted or mono- or polysubstituted, having 1 to 3 C atoms or 1 to 5 C atoms or 1 to 6 C atoms, i.e. $C_{1-3}$-alkanyls, $C_{2-3}$-alkenyls and $C_{2-3}$-alkynyls, or $C_{1-5}$-alkanyls, $C_{2-5}$-alkenyls and $C_{2-5}$-alkynyls, or $C_{1-6}$-alkanyls, $C_{2-6}$-alkenyls and $C_{2-6}$-alkynyls. In this context, alkenyls have at least one C—C double bond and alkynyls have at least one C—C triple bond. Alkyl is advantageously chosen from the group which includes methyl, ethyl, n-propyl, 2-propyl, n-butyl, iso-butyl, sec-butyl, tert-butyl, n-pentyl, iso-pentyl, neo-pentyl, hexyl, ethylenyl (vinyl), ethynyl, propenyl (—$CH_2CH=CH_2$, —CH=CH—$CH_3$, —C(=$CH_2$)—$CH_3$), propynyl (—CH—C≡CH, —C≡C—$CH_3$), butenyl, butynyl, pentenyl, pentynyl, hexenyl and hexynyl. Methyl, ethyl, n-propyl and iso-propyl are particularly advantageous.

For the purpose of this invention, the expression "cycloalkyl" or "$C_{3-8}$-cycloalkyl" denotes cyclic hydrocarbons having 3, 4, 5, 6, 7 or 8 carbon atoms, wherein the hydrocarbons can be saturated or unsaturated (but not aromatic), unsubstituted or mono- or polysubstituted. $C_{3-8}$-Cycloalkyl is advantageously chosen from the group which contains cyclopropyl, cyclobutyl, cyclopentyl, cyclohexyl, cycloheptyl, cyclooctyl, cyclopentenyl, cyclohexenyl, cycloheptenyl and cyclooctenyl.

The term "heterocyclyl" includes saturated or unsaturated (but not aromatic) cycloalkyls having three to eight ring members, in which one or two carbon atoms are replaced by a hetero atom S, N or O. Heterocyclyl radicals from the group tetrahydropyranyl, dioxanyl, dioxolanyl, morpholinyl, piperidinyl, piperazinyl, pyrazolinonyl and pyrrolidinyl are advantageous.

In the context of this invention, the expression "aryl" denotes aromatic hydrocarbons having up to 14 ring members, inter alia phenyls and naphthyls. The aryl radicals can also be condensed with further saturated, (partially) unsaturated or aromatic ring systems. Each aryl radical can be unsubstituted or mono- or polysubstituted, wherein the substituents on the aryl can be identical or different and can be in any desired and possible position of the aryl. Aryl is advantageously chosen from the group which contains phenyl, 1-naphthyl, 2-naphthyl, which can in each case be unsubstituted or mono- or polysubstituted.

The expression "heteroaryl" represents a 5-, 6- or 7-membered cyclic aromatic group which contains at least 1, if appropriate also 2, 3, 4 or 5 hetero atoms, wherein the hetero atoms are identical or different and the heterocyclic ring can be unsubstituted or mono- or polysubstituted; in the case of substitution on the heterocyclic ring, the substituents can be identical or different and can be in any desired and possible position of the heteroaryl. The heterocyclic ring can also be part of a bi- or polycyclic system having up to 14 ring members. Preferred hetero atoms are nitrogen, oxygen and sulfur. It is preferable for the heteroaryl radical to be chosen from the group which contains pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, indazolyl, purinyl, indolizinyl, quinolinyl, isoquinolinyl, quinazolinyl, carbazolyl, phenazinyl or oxadiazolyl, wherein bonding to the compounds corresponding to structure I can take place via any desired and possible ring member of the heteroaryl radical. Pyridyl, furyl and thienyl are particularly preferred.

For the purpose of the present invention, the expressions "aryl, heteroaryl, heterocyclyl or cycloalkyl bonded via $C_{1-3}$-alkyl" and "aryl, heteroaryl, heterocyclyl or cycloalkyl bonded via $C_{1-5}$-alkyl" mean that $C_{1-3}$-alkyl and aryl or heteroaryl or heterocyclyl or cycloalkyl have the meanings defined above and the aryl or heteroaryl or heterocyclyl or cycloalkyl radical is bonded to the compound corresponding to structure I via a $C_{1-3}$-alkyl group or a $C_{1-5}$-alkyl group. The alkyl chain can in all cases be saturated or unsaturated, branched or unbranched, unsubstituted or mono- or polysubstituted. It is advantageous if the alkyl chain is unsubstituted. Phenyl, benzyl and phenethyl are particularly advantageous in the context of this invention.

In connection with "alkyl", "heterocyclyl" and "cycloalkyl", in the context of this invention the term "substituted" is understood as meaning replacement of a hydrogen by F, Cl, Br, I, —CN, $NH_2$, $NH-C_{1-6}$-alkyl, $NH-C_{1-6}$-alkyl-OH, $C_{1-6}$-alkyl, $N(C_{1-6}$-alkyl$)_2$, $N(C_{1-6}$-alkyl-OH$)_2$, $NO_2$, SH, $S-C_{1-6}$-alkyl, S-benzyl, $O-C_{1-6}$-alkyl, OH, $O-C_{1-6}$-alkyl-OH, =O, O-benzyl, $C(=O)C_{1-6}$-alkyl, $CO_2H$, $CO_2-C_{1-6}$-alkyl, phenyl or benzyl, where polysubstituted radicals are to be understood as meaning those radicals which are substituted several times, e.g. two or three times, either on different or on the same atoms, for example three times on the same C atom, as in the case of $CF_3$ or $-CH_2CF_3$, or at different places, as in the case of $-CH(OH)-CH=CH-CHCl_2$. Polysubstitution can be by the same or by different substituents.

With respect to "aryl" and "heteroaryl", in the context of this invention "mono- or polysubstituted" means the replacement once or several times, e.g. two, three or four times, of one or more hydrogen atoms of the ring system by F, Cl, Br, I, CN, $NH_2$, $NH-C_{1-6}$-alkyl, $NH-C_{1-6}$-alkyl-OH, $N(C_{1-6}$-alkyl$)_2$, $N(C_{1-6}$-alkyl-OH$)_2$, $NO_2$, SH, $S-C_{1-6}$-alkyl, OH, $O-C_{1-6}$-alkyl, $O-C_{1-6}$alkyl-OH, $C(=O)C_{1-6}$-alkyl, $C(=O)NHC_{1-6}$-alkyl; $C(=O)$-aryl; $C(=O)-N$-morpholine; $C(=O)$-piperidine; $(C=O)$-pyrrolidine; $(C=O)$-piperazine; $NHSO_2C_{1-6}$-alkyl, $NHCOC_{1-6}$-alkyl, $CO_2H$, $CH_2SO_2$-phenyl, $CO_2-C_{1-6}$-alkyl, $OCF_3$, $CF_3$, $SCF_3$

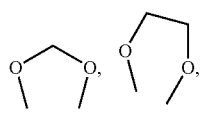

$C_{1-6}$-alkyl, pyrrolidinyl, piperidinyl, morpholinyl, benzyloxy, phenoxy, phenyl, pyridyl, alkylaryl, thienyl or furyl; on one or optionally various atoms, wherein a substituent can optionally be substituted in its turn, but not by a further aryl or heteroaryl ring. In this context, polysubstitution is by the same or by different substituents. Preferred substituents for "aryl" or "heteroaryl" are F, Cl, $OCH_3$, $CF_3$ and $CH_3$.

In the context of this invention, the term salt formed with a physiologically acceptable acid is understood as meaning salts of the particular active compound with inorganic or organic acids, which are physiologically acceptable—in particular when used on humans and/or mammals. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethylbenzoic acid, α-liponic acid, acetylglycine, hippuric acid, phosphoric acid and/or aspartic acid. Citric acid and hydrochloric acid are particularly preferred.

Substituted tetrahydropyrrolopyrazine compounds which are preferred in the context of this invention are those corresponding to formula I wherein $R^1$, $R^2$ and $R^3$ each independently represent hydrogen, $C_{1-6}$-alkyl, saturated or unsaturated, branched or unbranched, unsubstituted or mono- or polysubstituted; F, Cl, Br, I, CN, $NH_2$, $NH-C_{1-6}$-alkyl, $NH-C_{1-6}$-alkyl-OH, $N(C_{1-6}$-alkyl$)_2$, $N(C_{1-6}$-alkyl-OH$)_2$, NHaryl; NH-alkylaryl; NH-heteroaryl; $NO_2$, SH, $S-C_{1-6}$-alkyl, OH, $O-C_{1-6}$-alkyl, $O-C_{1-6}$alkyl-OH, $C(=O)C_{1-6}$-alkyl, $NHSO_2C_{1-6}$-alkyl, NHCOaryl; $NHCOC_{1-6}$-alkyl, $CO_2H$, $CH_2SO_2$-phenyl, $CO_2-C_{1-6}$-alkyl, $OCF_3$, $SCF_3$, $CF_3$, benzyloxy, morpholinyl, pyrrolidinyl, piperidinyl, piperazinyl, phenoxy, phenyl, pyridyl, alkylaryl, thienyl or furyl; or $R^1$ and $R^2$ or $R^2$ and $R^3$ form a ring and together denote

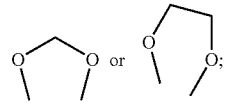

$R^4$ and $R^5$ each independently represent H, F, Cl, Br, I, $-CN$, $NH_2$, $NH-C_{1-6}$-alkyl, $NH-C_{1-6}$-alkyl-OH, $C_{1-6}$-alkyl, $N(C_{1-6}$-alkyl$)_2$, $N(C_{1-6}$-alkyl-OH$)_2$, $NO_2$, SH, $S-C_{1-6}$-alkyl, S-benzyl, $O-C_{1-6}$-alkyl, OH, $O-C_{1-6}$-alkyl-OH, O-benzyl, $C(=O)C_{1-6}$-alkyl, $CO_2H$, $CO_2-C_{1-6}$-alkyl or benzyl;

$R^6$ represents $C_{1-6}$-alkyl, branched or unbranched, unsubstituted or mono- or polysubstituted; aryl or heteroaryl, unsubstituted or mono- or polysubstituted; or an aryl or heteroaryl radical linked via a $C_{1-3}$-alkyl chain and unsubstituted or mono- or polysubstituted;

$R^{4a}$, $R^{5a}$ and $R^{6a}$ each independently represent H or $C_{1-6}$-alkyl;

$R^7$ represents $C(=O)R^{13}$;

$R^{13}$ denotes $C_{1-6}$-alkyl, saturated or unsaturated, branched or unbranched, unsubstituted or mono- or polysubstituted; aryl, heteroaryl or $C_{3-8}$-cycloalkyl, in each case unsubstituted or mono- or polysubstituted; or aryl, heteroaryl or $C_{3-8}$-cycloalkyl linked via a $C_{1-5}$-alkyl chain and in each case unsubstituted or mono- or polysubstituted, wherein the alkyl chain can be branched or unbranched, saturated or unsaturated;

with the provisos that if $R^1$-$R^5$ represent H and $R^6$ denotes $C_{1-6}$-alkyl or phenyl, unsubstituted or substituted once to three times by $C_{1-6}$-alkyl or $C_{1-6}$-alkoxy, $R^7$ does not denote $C_{1-5}$-alkyl-phenyl or $C_{1-5}$-alkyl linked via $C(=O)$;

if $R^6$ represents $CH_3$, $R^7$ does not denote $C(=O)CH_2CH_2$-imidazolyl; and if $R^6$ represents phenyl and $R^7$ represents $C(O)R^{13}$, $R^{13}$ does not denote 3-trifluoromethylphenyl, 3,4-dimethoxyphenyl, furanyl, 4-nitrophenyl or 4-methylphenyl;

wherein

"alkyl substituted", "heterocyclyl substituted" and "cycloalkyl substituted" represents the replacement of a hydrogen by F, Cl, Br, I, $-CN$, $NH_2$, $NH-C_{1-6}$-alkyl, $NH-C_{1-6}$-alkyl-OH, $C_{1-6}$-alkyl, $N(C_{1-6}$-alkyl$)_2$, $N(C_{1-6}$-alkyl-OH$)_2$, $NO_2$, SH, $S-C_{1-6}$-alkyl, S-benzyl, $O-C_{1-6}$-alkyl, OH, $O-C_{1-6}$-alkyl-OH, $=O$, O-benzyl, $C(=O)C_{1-6}$-alkyl, $CO_2H$, $CO_2-C_{1-6}$-alkyl, phenyl or benzyl; and "aryl substituted" and "heteroaryl substituted" represents the replacement once or several times, e.g. two, three or four times, of one or more hydrogen atoms of the ring system by F, Cl, Br, I, CN, $NH_2$, $NH-C_{1-6}$-alkyl, $NH-C_{1-6}$-alkyl-OH, $N(C_{1-6}$alkyl$)_2$, $N(C_{1-6}$-alkyl-OH$)_2$, $NO_2$, SH, $S-C_{1-6}$-alkyl, OH, $O-C_{1-6}$-alkyl, $O-C_{1-6}$alkyl-OH, $C(=O)$-aryl; $C(=O)C_{1-6}$-alkyl, $C(=O)NHC_{1-6}$-alkyl; $C(=O)-N$-morpholine; $C(=O)$-piperidine; $(C=O)$-pyrrolidine; $(C=O)$-piperazine; $NHSO_2C_{1-6}$-alkyl, $NHCOC_{1-6}$-alkyl, $CO_2H$, $CH_2SO_2$-phenyl, $CO_2-C_{1-6}$-alkyl, $OCF_3$, $SCF_3$, $CF_3$,

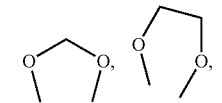

$C_{1-6}$-alkyl, pyrrolidinyl, piperidinyl, morpholinyl, benzyloxy, phenoxy, phenyl, pyridyl, alkylaryl, thienyl or furyl;

in the form of the racemate; of the enantiomers, diastereomers, mixtures of the enantiomers or diastereomers or of an individual enantiomer or diastereomer; of the bases and/or salts of physiologically acceptable acids.

Particularly preferred substituted tetrahydropyrrolopyrazines are those corresponding to formula I wherein $R^1$, $R^2$ and $R^3$ each independently represent hydrogen or $C_{1-6}$-alkyl, branched or unbranched, in particular H.

Particularly preferred substituted tetrahydropyrrolopyrazines are also those corresponding to formula I wherein $R^4$ and $R^5$ each independently represent H or $C_{1-6}$-alkyl, in particular H.

Substituted tetrahydropyrrolopyrazines which are furthermore particularly preferred are also those corresponding to formula I wherein $R^6$ represents methyl, ethyl, isopropyl, n-propyl, n-butyl, sec-butyl, tert-butyl, iso-butyl; phenyl, naphthyl, thienyl, furyl, pyrrolyl, indolyl, benzofuranyl, benzothienyl, benzothiadiazolyl, benzothiazolyl, benzodioxolanyl, benzodioxanyl, pyrazolyl, imidazolyl, thiazolyl, oxadiazolyl, isoxazolyl, pyridyl, pyridazinyl, pyrimidinyl, pyrazinyl, purinyl, quinolinyl, isoquinolinyl, quinazolinyl, oxadiazolyl, unsubstituted or mono- or polysubstituted; benzyl or phenethyl, unsubstituted or mono- or polysubstituted. In particular, $R^6$ represents methyl, ethyl, isopropyl, n-propyl, n-butyl, sec-butyl, tert-butyl, iso-butyl; phenyl, naphthyl, thienyl, furyl or benzyl, unsubstituted or mono- or polysubstituted.

Preferably, $R^{4a}$, $R^{5a}$ and $R^{6a}$ denote hydrogen.

Preferred substituted tetrahydropyrrolopyrazines are moreover those corresponding to formula I wherein $R^7$ represents $C(=O)R^{13}$. Particularly preferred substituted tetrahydropyrrolopyrazines are those wherein $R^{13}$ denotes $C_{1-6}$-alkyl, saturated or unsaturated, branched or unbranched, unsubstituted or mono- or polysubstituted; phenyl or naphthyl, in each case unsubstituted or mono- or polysubstituted; cyclopropyl, cyclobutyl, cyclopentyl or cyclohexyl, in each case unsubstituted or mono- or polysubstituted; furanyl, thienyl or pyridyl, in each case unsubstituted or mono- or polysubstituted; or phenyl, naphthyl, cyclopropyl, cyclobutyl, cyclopentyl, cyclohexyl, furanyl, thienyl or pyridyl linked via a $C_{1-5}$-alkyl chain and in each case unsubstituted or mono- or polysubstituted, wherein the alkyl chain can be branched or unbranched, saturated or unsaturated. In particular, $R^{13}$ denotes $C_{1-6}$-alkyl, saturated or unsaturated, branched or unbranched, unsubstituted or mono- or polysubstituted by $OCH_3$ or OH; phenyl or naphthyl, in each case unsubstituted or mono- or polysubstituted by F, Cl,

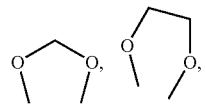

$CH_3$, $CF_3$, t-butyl, $OCF_3$ or $SCF_3$; cyclopropyl, cyclobutyl, cyclopentyl or cyclohexyl; furanyl, thienyl or pyridyl, in each case unsubstituted or mono- or polysubstituted by $CH_3$, F, Cl or $CF_3$; or phenethyl, phenethenyl, propylphenyl, propenylphenyl, butylphenyl, butenylphenyl or benzyl, in each case unsubstituted or mono- or polysubstituted by F, Cl, $CH_3$, $CF_3$, $OCF_3$ or $SCF_3$, wherein the alkyl chain can be branched or unbranched, saturated or unsaturated.

The most preferred substituted tetrahydropyrrolopyrazines are those selected from the group consisting of:

1 (3-fluorophenyl)(1-(2-methoxyphenyl)-3,4-dihydropyrrolo[1,2-a]pyrazin-2(1H)-yl)methanone;
2 cyclopentyl-[1-(2-methoxy-phenyl)-3,4-dihydro-1H-pyrrolo[1,2-a]pyrazin-2-yl]-methanone;
3 benzo[1,3]dioxol-5-yl-[1-(2-methoxy-phenyl)-3,4-dihydro-1H-pyrrolo[1,2-a]pyrazin-2-yl]-methanone;
4 (2-methoxy-phenyl)-[1-(2-methoxy-phenyl)-3,4-dihydro-1H-pyrrolo[1,2-a]pyrazin-2-yl]-methanone;
5 (1-(2-fluorophenyl)-3,4-dihydropyrrolo[1,2-a]pyrazin-2(1H)-yl)(furan-2-yl)methanone;
6 cyclopropyl(1-(2-fluorophenyl)-3,4-dihydropyrrolo[1,2-a]pyrazin-2(1H)-yl)methanone;
7 (3-fluoro-phenyl)-[1-(2-fluoro-phenyl)-3,4-dihydro-1H-pyrrolo[1,2-a]pyrazin-2-yl]-methanone;
8 (1-(2-fluorophenyl)-3,4-dihydropyrrolo[1,2-a]pyrazin-2(1H)-yl)(o-tolyl)methanone;
9 benzo[d][1,3]dioxol-5-yl(1-(2-fluorophenyl)-3,4-dihydropyrrolo[1,2-a]pyrazin-2(1H)-yl)methanone];
10 cyclopentyl-(1-o-tolyl-3,4-dihydro-1H-pyrrolo[1,2-a]pyrazin-2-yl)-methanone;
11 o-tolyl(1-o-tolyl-3,4-dihydropyrrolo[1,2-a]pyrazin-2(1H)-yl)methanone;
12 benzo[d][1,3]dioxol-5-yl(1-o-tolyl-3,4-dihydropyrrolo[1,2-a]pyrazin-2(1H)-yl)methanone;
13 (4-fluoro-phenyl)-(1-m-tolyl-3,4-dihydro-1H-pyrrolo[1,2-a]pyrazin-2-yl)-methanone;
14 thiophen-2-yl(1-m-tolyl-3,4-dihydropyrrolo[1,2-a]pyrazin-2(1H)-yl)methanone;
16 (3-fluoro-phenyl)-(1-m-tolyl-3,4-dihydro-1H-pyrrolo[1,2-a]pyrazin-2-yl)-methanone;
17 cyclopentyl(1-m-tolyl-3,4-dihydropyrrolo[1,2-a]pyrazin-2(1H)-yl)methanone;
18 benzo[1,3]dioxol-5-yl-(1-m-tolyl-3,4-dihydro-1H-pyrrolo[1,2-a]pyrazin-2-yl)-methanone;
19 (1-(2,4-difluorophenyl)-3,4-dihydropyrrolo[1,2-a]pyrazin-2(1H)-yl)(4-fluorophenyl)methanone;
20 (4-fluorophenyl)(1-phenyl-3,4-dihydropyrrolo[1,2-a]pyrazin-2(1H)-yl)methanone;
22 (1-phenyl-3,4-dihydropyrrolo[1,2-a]pyrazin-2(1H)-yl)(thiophen-2-yl)methanone;
23 (3-fluorophenyl)(1-phenyl-3,4-dihydropyrrolo[1,2-a]pyrazin-2(1H)-yl)methanone;
24 cyclopentyl(1-phenyl-3,4-dihydropyrrolo[1,2-a]pyrazin-2(1H)-yl)methanone;
25 2-methoxy-1-(1-phenyl-3,4-dihydropyrrolo[1,2-a]pyrazin-2(1H)-yl)methanone;
26 (1-phenyl-3,4-dihydropyrrolo[1,2-a]pyrazin-2(1H)-yl)(o-tolyl)methanone;
27 (2-methoxyphenyl)(1-phenyl-3,4-dihydropyrrolo[1,2-a]pyrazin-2(1H)-yl)methanone;
28 cyclobutyl(1-(4-fluorophenyl)-3,4-dihydropyrrolo[1,2-a]pyrazin-2(1H)-yl)methanone;
29 (1-(4-chlorophenyl)-3,4-dihydropyrrolo[1,2-a]pyrazin-2(1H)-yl)(2-methoxyphenyl)methanone;
30 furan-2-yl(1-(3-methoxyphenyl)-3,4-dihydropyrrolo[1,2-a]pyrazin-2(1H)-yl)methanone;
32 (2-fluorophenyl)(1-o-tolyl-3,4-dihydropyrrolo[1,2-a]pyrazin-2(1H)-yl)methanone;
33 benzo[1,3]dioxol-5-yl-[1-(2,3-dihydro-benzo[1,4]dioxin-6-yl)-3,4-dihydro-1H-pyrrolo[1,2-a]pyrazin-2-yl]-methanone;
34 [1-(2,3-dihydro-benzo[1,4]dioxin-6-yl)-3,4-dihydro-1H-pyrrolo[1,2-a]pyrazin-2-yl]-o-tolyl-methanone;

35 [1-(2,3-dihydro-benzo[1,4]dioxin-6-yl)-3,4-dihydro-1H-pyrrolo[1,2-a]pyrazin-2-yl]-(2-fluoro-phenyl)-methanone;
36 [1-(2,3-dihydro-benzo[1,4]dioxin-6-yl)-3,4-dihydro-1H-pyrrolo[1,2-a]pyrazin-2-yl]-thiophen-2-yl-methanone;
37 [1-(2,3-dihydro-benzo[1,4]dioxin-6-yl)-3,4-dihydro-1H-pyrrolo[1,2-a]pyrazin-2-yl]-furan-2-yl-methanone;
38 [1-(2,3-dihydro-benzo[1,4]dioxin-6-yl)-3,4-dihydro-1H-pyrrolo[1,2-a]pyrazin-2-yl]-(4-fluoro-phenyl)-methanone;
39 (1-(3-chlorophenyl)-3,4-dihydropyrrolo[1,2-a]pyrazin-2(1H)-yl)(2-methoxyphenyl)methanone;
40 benzo[d][1,3]dioxol-5-yl(1-(3-chlorophenyl)-3,4-dihydropyrrolo[1,2-a]pyrazin-2(1H)-yl)methanone;
41 (1-(3-chlorophenyl)-3,4-dihydropyrrolo[1,2-a]pyrazin-2(1H)-yl)(o-tolyl)methanone;
42 (1-(3-chlorophenyl)-3,4-dihydropyrrolo[1,2-a]pyrazin-2(1H)-yl)(cyclopentyl)methanone;
43 [1-(3-chloro-phenyl)-3,4-dihydro-1H-pyrrolo[1,2-a]pyrazin-2-yl]-(3-fluoro-phenyl)-methanone;
44 [1-(3-chloro-phenyl)-3,4-dihydro-1H-pyrrolo[1,2-a]pyrazin-2-yl]-(2-fluoro-phenyl)-methanone;
45 [1-(3-chloro-phenyl)-3,4-dihydro-1H-pyrrolo[1,2-a]pyrazin-2-yl]-thiophen-2-yl-methanone;
46 [1-(3-chloro-phenyl)-3,4-dihydro-1H-pyrrolo[1,2-a]pyrazin-2-yl]-(4-fluoro-phenyl)-methanone;
47 (2-fluorophenyl)(1-(2-fluorophenyl)-3,4-dihydropyrrolo[1,2-a]pyrazin-2(1H)-yl)methanone;
49 (2-fluorophenyl)(1-(2-methoxyphenyl)-3,4-dihydropyrrolo[1,2-a]pyrazin-2(1H)-yl)methanone;
50 (1-(4-(dimethylamino)phenyl)-3,4-dihydropyrrolo[1,2-a]pyrazin-2(1H)-yl)(o-tolyl)methanone;
51 (1-(4-(dimethylamino)phenyl)-3,4-dihydropyrrolo[1,2-a]pyrazin-2(1H)-yl)(2-fluorophenyl)methanone;
52 cyclopropyl(1-(4-(dimethylamino)phenyl)-3,4-dihydropyrrolo[1,2-a]pyrazin-2(1H)-yl)methanone;
53 (1-(4-(dimethylamino)phenyl)-3,4-dihydropyrrolo[1,2-a]pyrazin-2(1H)-yl)(thiophen-2-yl)methanone;
54 (1-(4-(dimethylamino)phenyl)-3,4-dihydropyrrolo[1,2-a]pyrazin-2(1H)-yl)(4-fluorophenyl)methanone;
55 2-methoxy-1-(1-(thiophen-2-yl)-3,4-dihydropyrrolo[1,2-a]pyrazin-2(1H)-yl)butan-1-one;
56 benzo[1,3]dioxol-5-yl-(1-thiophen-2-yl-3,4-dihydro-1H-pyrrolo[1,2-a]pyrazin-2-yl)-methanone;
57 (1-(thiophen-2-yl)-3,4-dihydropyrrolo[1,2-a]pyrazin-2(1H)-yl)(o-tolyl)methanone;
58 (3-fluoro-phenyl)-(1-thiophen-2-yl-3,4-dihydro-1H-pyrrolo[1,2-a]pyrazin-2-yl)-methanone;
59 cyclopropyl(1-(thiophen-2-yl)-3,4-dihydropyrrolo[1,2-a]pyrazin-2(1H)-yl)methanone;
60 (4-fluorophenyl)(1-(thiophen-2-yl)-3,4-dihydropyrrolo[1,2-a]pyrazin-2(1H)-yl)methanone;
61 benzo[1,3]dioxol-5-yl-[1-(3,4-dichloro-phenyl)-3,4-dihydro-1H-pyrrolo[1,2-a]pyrazin-2-yl]-methanone;
62 cyclopentyl-[1-(3,4-dichloro-phenyl)-3,4-dihydro-1H-pyrrolo[1,2-a]pyrazin-2-yl]-methanone;
63 [1-(3,4-dichloro-phenyl)-3,4-dihydro-1H-pyrrolo[1,2-a]pyrazin-2-yl]-(2-fluoro-phenyl)-methanone;
64 1-(1-(3,4-dichlorophenyl)-3,4-dihydropyrrolo[1,2-a]pyrazin-2(1H)-yl)-3-methylbutan-1-one;
65 (1-(3,4-Dichlorophenyl)-3,4-dihydropyrrolo[1,2-a]pyrazin-2(1H)-yl)(thiophen-2-yl)methanone;
66 cyclobutyl(1-(3,4-dichlorophenyl)-3,4-dihydropyrrolo[1,2-a]pyrazin-2(1H)-yl)methanone;
67 1-(1-(3,4-dichlorophenyl)-3,4-dihydropyrrolo[1,2-a]pyrazin-2(1H)-yl)-2-methylpropan-1-one;
68 [1-(3,4-dichloro-phenyl)-3,4-dihydro-1H-pyrrolo[1,2-a]pyrazin-2-yl]-furan-2-yl-methanone;
69 (2-fluorophenyl)(1-p-tolyl-3,4-dihydropyrrolo[1,2-a]pyrazin-2(1H)-yl)methanone;
70 (3-methylthiophen-2-yl)(1-phenyl-3,4-dihydropyrrolo[1,2-a]pyrazin-2(1H)-yl)methanone;
71 3-(2,4-difluorophenyl)-1-(1-phenyl-3,4-dihydropyrrolo[1,2-a]pyrazin-2(1H)-yl)prop-2-en-1-one;
72 3-phenyl-1-(1-(thiophen-2-yl)-3,4-dihydropyrrolo[1,2-a]pyrazin-2(1H)-yl)prop-2-en-1-one;
73 3-(4-fluorophenyl)-1-(1-methyl-3,4-dihydropyrrolo[1,2-a]pyrazin-2(1H)-yl)prop-2-en-1-one;
74 1-(1-methyl-3,4-dihydropyrrolo[1,2-a]pyrazin-2(1H)-yl)-3-(4-(trifluoromethylthio)phenyl)prop-2-en-1-one;
75 (1-(4-fluorophenyl)-3,4-dihydropyrrolo[1,2-a]pyrazin-2(1H)-yl)(o-tolyl)methanone;
76 3-phenyl-1-(1-(thiophen-2-yl)-3,4-dihydropyrrolo[1,2-a]pyrazin-2(1H)-yl)propan-1-one;
77 5-phenyl-1-(1-(thiophen-2-yl)-3,4-dihydropyrrolo[1,2-a]pyrazin-2(1H)-yl)pentan-1-one;
78 1-(1-(thiophen-2-yl)-3,4-dihydropyrrolo[1,2-a]pyrazin-2(1H)-yl)hexan-1-one;
82 phenyl(1-(thiophen-2-yl)-3,4-dihydropyrrolo[1,2-a]pyrazin-2(1H)-yl)methanone;
83 1-(1-(thiophen-2-yl)-3,4-dihydropyrrolo[1,2-a]pyrazin-2(1H)-yl)ethanone;
84 2-phenyl-1-(1-(thiophen-2-yl)-3,4-dihydropyrrolo[1,2-a]pyrazin-2(1H)-yl)ethanone;
85 3,3-dimethyl-1-(1-(thiophen-2-yl)-3,4-dihydropyrrolo[1,2-a]pyrazin-2(1H)-yl)butan-1-one;
86 3-cyclohexyl-1-(1-(thiophen-2-yl)-3,4-dihydropyrrolo[1,2-a]pyrazin-2(1H)-yl)propan-1-one, and
87 4-phenyl-1-(1-(thiophen-2-yl)-3,4-dihydropyrrolo[1,2-a]pyrazin-2(1H)-yl)butan-1-one.

The substituted tetrahydropyrrolopyrazine compounds according to the invention and their respective corresponding acids, bases, salts and solvates are suitable as pharmaceutical active compounds in pharmaceutical compositions.

The present invention therefore also provides a pharmaceutical composition containing at least one substituted tetrahydropyrrolopyrazine compound corresponding to formula I according to the invention, wherein $R^1$-$R^7$ have the above-mentioned meaning, and where appropriate one or more pharmaceutically acceptable auxiliary substances.

These pharmaceutical compositions according to the invention are suitable for influencing the reuptake of serotonin and/or noradrenaline. This also relates to compounds of which the structure is indeed already known, but of which the suitability as a pharmaceutical composition is unknown. The invention therefore also provides pharmaceutical compositions containing at least one compound corresponding to formula I

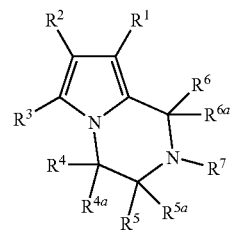

wherein

R$^1$, R$^2$ and R$^3$ each independently represent hydrogen, C$_{1-6}$-alkyl, saturated or unsaturated, branched or unbranched, unsubstituted or mono- or polysubstituted; F, Cl, Br, I, CN, NH$_2$, NH—C$_{1-16}$-alkyl, NH—C$_{1-6}$-alkyl-OH, N(C$_{1-6}$alkyl)$_2$, N(C$_{1-6}$-alkyl-OH)$_2$, NHaryl; NH-alkylaryl; NH-heteroaryl; NO$_2$, SH, S—C$_{1-6}$-alkyl, OH, O—C$_{1-6}$-alkyl, O—C$_{1-6}$alkyl-OH, C(=O)C$_{1-6}$-alkyl, NHSO$_2$C$_{1-6}$-alkyl, NHCOaryl; NHCOC$_{1-6}$-alkyl, CO$_2$H, CH$_2$SO$_2$-phenyl, CO$_2$—C$_{1-6}$-alkyl, OCF$_3$, SCF$_3$, CF$_3$, benzyloxy, morpholinyl, pyrrolidinyl, piperidinyl, piperazinyl, phenoxy, phenyl, pyridyl, alkylaryl, thienyl or furyl; or R$^1$ and R$^2$ or R$^2$ and R$^3$ form a ring and together denote

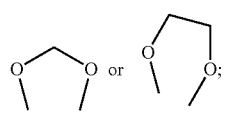

R$^4$ and R$^5$ each independently represent H, F, Cl, Br, I, —CN, NH$_2$, NH—C$_{1-6}$-alkyl, NH—C$_{1-6}$-alkyl-OH, C$_{1-6}$-alkyl, N(C$_{1-6}$-alkyl)$_2$, N(C$_{1-6}$-alkyl-OH)$_2$, NO$_2$, SH, S—C$_{1-6}$-alkyl, S-benzyl, O—C$_{1-6}$-alkyl, OH, O—C$_{1-6}$-alkyl-OH, O-benzyl, C(=O)C$_{1-6}$-alkyl, CO$_2$H, CO$_2$—C$_{1-6}$-alkyl or benzyl;

R$^6$ represents C$_{1-6}$-alkyl, branched or unbranched, unsubstituted or mono- or polysubstituted; aryl or heteroaryl, unsubstituted or mono- or polysubstituted; or an aryl or heteroaryl radical linked via a C$_{1-3}$-alkyl chain and unsubstituted or mono- or polysubstituted;

R$^{4a}$, R$^{5a}$ and R$^{6a}$ each independently represent H or C$_{1-6}$-alkyl;

R$^7$ represents C(=O)R$^{13}$;

R$^{13}$ denotes C$_{1-6}$-alkyl, saturated or unsaturated, branched or unbranched, unsubstituted or mono- or polysubstituted; aryl, heteroaryl or C$_{3-8}$-cycloalkyl, in each case unsubstituted or mono- or polysubstituted; or aryl, heteroaryl or C$_{3-8}$-cycloalkyl linked via a C$_{1-5}$-alkyl chain and in each case unsubstituted or mono- or polysubstituted, wherein the alkyl chain can be branched or unbranched, saturated or unsaturated;

in the form of the racemate; of the enantiomers, diastereomers, mixtures of the enantiomers or diastereomers or of an individual enantiomer or diastereomer; of the bases and/or salts of physiologically acceptable acids.

In connection with "phenyl", "phenyloxy", "benzyl", "benzyloxy", "alkylaryl", the term in each case includes the unsubstituted structure and the structure substituted by F, Cl, OCH$_3$, OCF$_3$, SCF$_3$ and CF$_3$ and CH$_3$.

Preferred pharmaceutical compositions are those corresponding to formula I wherein R$^1$ to R$^7$ have the meaning given in the preferred ranges disclosed above.

Particularly preferred pharmaceutical compositions are those containing active compounds selected from the group consisting of:

15 3-methyl-1-(1-m-tolyl-3,4-dihydropyrrolo[1,2-a]pyrazin-2(1H)-yl)butan-1-one;

21 furan-2-yl(1-phenyl-3,4-dihydropyrrolo[1,2-a]pyrazin-2(1H)-yl)methanone;

31 2-methyl-1-(1-o-tolyl-3,4-dihydropyrrolo[1,2-a]pyrazin-2(1H)-yl)butan-1-one, and 48 1-(1-(2-methoxyphenyl)-3,4-dihydropyrrolo[1,2-a]pyrazin-2(1H)-yl)-2-methylbutan-1-one, in the form of the racemate; of the enantiomers, diastereomers, mixtures of the enantiomers or diastereomers or of an individual enantiomer or diastereomer; of the bases and/or salts of physiologically acceptable acids.

The pharmaceutical compositions according to the invention are suitable for treatment of disorders or diseases which are at least partly mediated by the reuptake of serotonin or noradrenaline. The pharmaceutical compositions according to the invention are particularly suitable for treatment of pain, depression, anxiety states, fibromyalgia, eating disorders, bulimia, hyperactivity (attention deficit hyperactivity disorder; ADHD), drug dependency, addiction and withdrawal, trichotillomania, skin diseases, such as postherpetic neuralgia and pruritus, memory disorders, cognitive disorders and Alzheimer's disease. The pharmaceutical compositions of the invention are especially suitable for treating or inhibiting pain, in particular chronic and/or neuropathic pain, depression and anxiety states.

The present invention also provides the use of at least one substituted tetrahydropyrrolopyrazine compound according to the invention and where appropriate of one or more pharmaceutically acceptable auxiliary substances for the preparation of a pharmaceutical composition for treatment of disorders or diseases which are at least partly mediated by the reuptake of serotonin or noradrenaline.

The use of at least one substituted tetrahydropyrrolopyrazine compound according to the invention and where appropriate of one or more pharmaceutically acceptable auxiliary substances for the preparation of a pharmaceutical composition for treatment of pain, depression, anxiety states, fibromyalgia, eating disorders, bulimia, hyperactivity (attention deficit hyperactivity disorder; ADHD), drug dependency, addiction and withdrawal, trichotillomania, skin diseases, such as postherpetic neuralgia and pruritus, memory disorders, cognitive disorders and Alzheimer's disease is preferred.

The use of at least one substituted tetrahydropyrrolopyrazine compound according to the invention and where appropriate of one or more pharmaceutically acceptable auxiliary substances for the preparation of a pharmaceutical composition for treatment of pain, in particular chronic and/or neuropathic pain, depression and anxiety states is particularly preferred.

The present invention also provides a process for the preparation of the substituted tetrahydropyrrolopyrazine compounds according to the invention. The chemicals and reaction components employed in the reactions described below are commercially obtainable or can in each case be prepared by conventional methods known to the person skilled in the art.

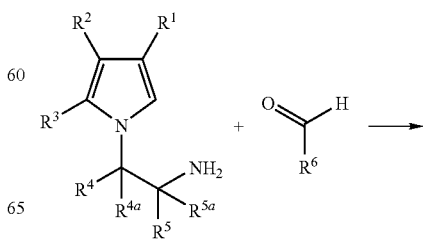

-continued

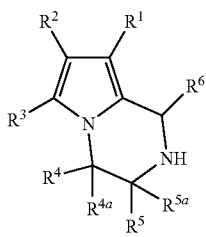

In this reaction, a solution of the optionally substituted 2-(1H-pyrrol-1-yl)ethanamine and of the aldehyde corresponding to formula $R^6C(=O)H$ is:

a) stirred in an organic acid, for example acetic acid, at room temperature for from 6 to 48 hours; or
b) stirred in an alcohol, for example ethanol or methanol, with the addition of an organic acid, for example acetic acid or citric acid, at a temperature of 0-100° C., preferably 20° C. to 78° C., for from 2 to 48 hours; or
c) treated in an organic solvent, for example toluene, benzene or MC, with benzotriazole and an acid, for example p-toluenesulfonic acid, and refluxed using a water separator.

After removal of the solvent, the residue can be taken up in an aqueous basic solution, for example sodium carbonate solution, sodium bicarbonate solution, potassium carbonate solution, sodium hydroxide solution or potassium hydroxide solution, and the solution can be extracted with an organic solvent, for example MC, chloroform, ethyl acetate or diethyl ether. Alternatively, the residue can be taken up in an organic solvent, for example ethyl acetate, MC, chloroform or diethyl ether. The organic phase can be washed with an aqueous basic solution, for example sodium carbonate solution, sodium bicarbonate solution, potassium carbonate solution, sodium hydroxide solution or potassium hydroxide solution.

For the subsequent acylation reaction, an acid can be reacted with the corresponding tetrahydropyrrolopyrazine with the addition of a base, for example diisopropylamine, triethylamine or diisopropylethylamine, and a coupling reagent, for example EDCI or CDI, and optionally hydroxybenzotriazole hydrate, in an organic solvent, for example MC or THF, at 0-100° C., preferably 20° C. to 69° C.

Alternatively, a tetrahydropyrrolopyrazine can be reacted with an acid chloride with the addition of a base, for example triethylamine, diisopropylethylamine or diisopropylamine, in an organic solvent, for example DCE or MC, at a temperature of 0-100° C., preferably 20° C. to 80° C.

When the reaction has ended, the mixture can be rendered basic with a solution of an inorganic base, for example sodium carbonate, sodium bicarbonate, potassium carbonate, sodium hydroxide or potassium hydroxide. The organic phase can then be separated off, washed with water and concentrated. For purification, suitable scavenger resins can be used, or the crude product can be subjected to acidic extraction after addition of a suitable solvent, such as, for example, MC, chloroform, ethyl acetate or diethyl ether.

The reactions described above can furthermore in each case be carried out under conventional conditions familiar to the person skilled in the art, for example with respect to pressure, temperature, inert gas atmosphere or sequence of the addition of the components. If appropriate, the optimum process procedure under the particular conditions can be ascertained by the person skilled in the art by simple preliminary experiments.

All the process steps described above and in each case also the purification and/or isolation of intermediate or end products can be carried out partly or completely under an inert gas atmosphere, preferably under a nitrogen atmosphere or argon atmosphere.

The substituted tetrahydropyrrolopyrazine compounds according to the invention can be isolated either in the form of their free bases, their free acids, or also in each case in the form of corresponding salts, in particular physiologically acceptable salts.

The free bases of the particular substituted tetrahydropyrrolopyrazine compounds according to the invention can be converted, for example, by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, maleic acid, malic acid, succinic acid, tartaric acid, mandelic acid, fumaric acid, lactic acid, citric acid, glutamic acid or aspartic acid, into the corresponding salts, preferably physiologically acceptable salts.

The free bases of the particular substituted tetrahydropyrrolopyrazine compounds according to the invention can likewise by converted with the free acid or a salt of a sugar substitute, such as e.g. saccharin, cyclamate or acesulfame, into the corresponding physiologically acceptable salts.

The free acids of the substituted tetrahydropyrrolopyrazine compounds according to the invention can correspondingly be converted by reaction with a suitable base into the corresponding physiologically acceptable salts. Examples of suitable salts include the alkali metal salts, alkaline earth metal salts or ammonium salts $[NH_xR_{4-x}]^+$, wherein x=0, 1, 2, 3 or 4 and R represents a linear or branched $C_{1-4}$-alkyl group.

Where appropriate, the substituted tetrahydropyrrolopyrazine compounds according to the invention can also be obtained, like the corresponding acids, the corresponding bases or salts of these compounds, in the form of their solvates, preferably in the form of their hydrate, by conventional methods known to persons skilled in the art.

If the substituted tetrahydropyrrolopyrazine compounds according to the invention are obtained in the form of a mixture of their stereoisomers, preferably in the form of their racemates or other mixtures of their various enantiomers and/or diastereomers, after their preparation, these can be separated and optionally isolated by conventional methods known to the person skilled in the art. There may be mentioned by way of example chromatography separation methods, in particular liquid chromatography methods under normal pressure or under increased pressure, preferably MPLC and HPLC methods, and methods of fractional crystallization. In this context, in particular individual enantiomers, e.g. diastereomeric salts formed by means of HPLC on a chiral stationary phase or by means of crystallization with chiral acids, for example (+)-tartaric acid, (−)-tartaric acid or (+)-10-camphorsulfonic acid, can be separated from one another.

The pharmaceutical compositions according to the invention can be in a liquid, semisolid or solid pharmaceutical composition form, for example in the form of injection solutions, drops, juices, syrups, sprays, suspensions, tablets, patches, capsules, plasters, suppositories, ointments, creams, lotions, gels, emulsions, aerosols or in a multiparticulate form, for example in the form of pellets or granules, optionally pressed to tablets, filled in capsules or suspended in a liquid, and can also be administered as such. In addition to at least one substituted tetrahydropyrrolopyrazine compound according to the invention, the pharmaceutical composition according to the invention conventionally contains further physiologically acceptable pharmaceutical auxiliary substances, which can preferably be chosen from the group consisting of carrier materials, fillers, solvents, diluents, surface-active substances, dyestuffs, preservatives, disintegrating agents, slip agents, lubricants, aromas and binders.

The choice of physiologically acceptable auxiliary substances and the amounts thereof to be employed depends on whether the pharmaceutical composition is to be administered orally, subcutaneously, parenterally, intravenously, intraperitoneally, intradermally, intramuscularly, intranasally, buccally, rectally or locally, for example on infections on the skin, the mucous membranes or on the eyes. Formulations in the form of tablets, coated tablets, capsules, granules, pellets, drops, juices and syrups are preferably suitable for oral administration, and solutions, suspensions, easily reconstitutable dry formulations and sprays are suitable for parenteral, topical and inhalatory administration.

The substituted tetrahydropyrrolopyrazine compounds employed in the pharmaceutical compositions according to the invention can be in a depot, in dissolved form or in a plaster, optionally with the addition of agents which promote penetration through the skin, as suitable formulations for percutaneous administration.

Formulation forms which can be used orally or percutaneously can also release the particular substituted tetrahydropyrrolopyrazine compound according to the invention in a delayed manner.

The pharmaceutical compositions according to the invention are prepared with the aid of conventional agents, devices, methods and processes known from the prior art, such as are described, for example, in "Remingtons Pharmaceutical Sciences", editor A. R. Gennaro, 17th edition, Mack Publishing Company, Easton, Pa., 1985, in particular in part 8, chapter 76 to 93. The corresponding description is introduced herewith as reference and is part of the disclosure.

The amount of the particular substituted tetrahydropyrrolopyrazine compound according to the invention to be administered to patients can vary and depends, for example, on the weight or age of the patient and on the mode of administration, the indication and the severity of the disease. 0.005 to 100 mg/kg, preferably 0.05 to 75 mg/kg of body weight of the patient of at least one such compound according to the invention are conventionally administered.

The invention will be explained in further detail hereinafter with reference to some illustrative examples. These examples are given merely for purposes of illustration and do not limit the general inventive idea.

Examples

In the examples, $R^{4a}$, $R^{5a}$ and $R^{6a}$ in each case denote H.

Synthesis of the Example Compounds

Synthesis of the
1-aryl-1,2,3,4-tetrahydropyrrolo[1,2-a]pyrazines

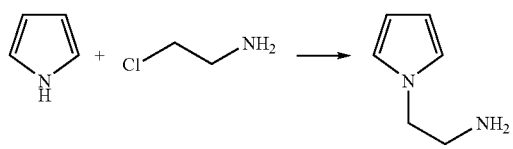

NaOH (9.4 g; 0.23 mol) and tetrabutylammonium hydrogen sulfate (0.8 g; 2.36 mmol) were added to a solution of pyrrole (0.06 mol) in acetonitrile (33 ml) and the mixture was stirred at room temperature for 30 minutes. After addition of 2-chloroethylamine hydrochloride (8.2 g; 0.07 mol), the mixture was heated under reflux for 24 h. After cooling, the insoluble inorganic residue was filtered off and the solvent was removed under reduced pressure. The crude product was obtained and was used for further reactions without further purification.

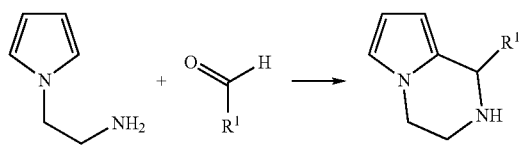

Method A

A solution of 2-(1H-pyrrol-1-yl)ethanamine (0.1 mol) and of the corresponding aldehyde (0.1 mol) in acetic acid (250 ml) was stirred at room temperature for 48 h. When the reaction had ended, the solvent was removed on a rotary evaporator, the residue was taken up in aqueous sodium carbonate solution (10%) and the mixture was extracted with MC. The organic phase was then dried over $MgSO_4$ and concentrated in vacuo. Purification was carried out by column chromatography on neutral $Al_2O_3$ or by washing with 2-propanol or by crystallization with 2-propanol/n-hexane.

Method B

Acetic acid (0.3 ml) was added to a solution of 2-(1H-pyrrol-1-yl)ethanamine (0.05 mol) and of the corresponding aldehyde (0.05 mol) in ethanol (25 ml) and the mixture was heated under reflux for 10 min. The mixture was then subsequently stirred at room temperature for a further 1 h. The reaction mixture was concentrated on a rotary evaporator and the residue was taken up in ethyl acetate. The organic phase was washed with $NaHCO_3$ solution, dried over $MgSO_4$ and concentrated. Purification was carried out by column chromatography on neutral $Al_2O_3$.

The following tetrahydropyrrolopyrazines were used for synthesis of the example compounds:

| No. | Name | Structure | Method |
|---|---|---|---|
| AM1 | 1-(3-methoxyphenyl)-1,2,3,4-tetrahydropyrrolo[1,2-a]pyrazine | 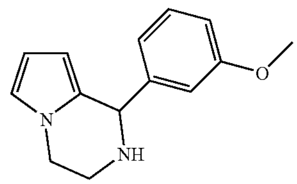 | B |
| AM2 | 1-phenyl-1,2,3,4-tetrahydropyrrolo[1,2-a]pyrazine | 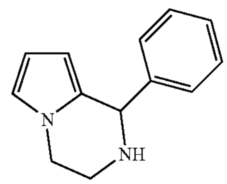 | A |
| AM3 | 1-(thiophen-2-yl)-1,2,3,4-tetrahydropyrrolo[1,2-a]pyrazine | 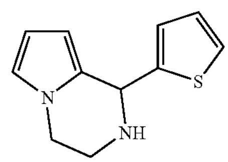 | B |
| AM4 | 1-(3-fluorophenyl)-1,2,3,4-tetrahydropyrrolo[1,2-a]pyrazine | 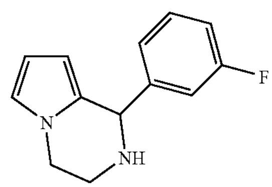 | B |
| AM5 | 1-p-tolyl-1,2,3,4-tetrahydropyrrolo[1,2-a]pyrazine | 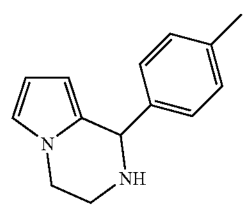 | A |
| AM6 | 1-(4-chlorophenyl)-1,2,3,4-tetrahydropyrrolo[1,2-a]pyrazine | 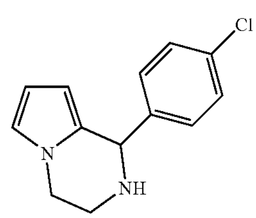 | A |
| AM7 | 1-(4-fluorophenyl)-1,2,3,4-tetrahydropyrrolo[1,2-a]pyrazine | 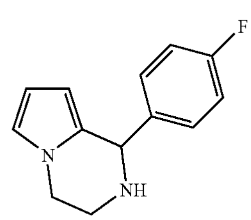 | A |

-continued

| No. | Name | Structure | Method |
|---|---|---|---|
| AM8 | 1-(2,4-difluorophenyl)-1,2,3,4-tetrahydropyrrolo[1,2-a]pyrazine | 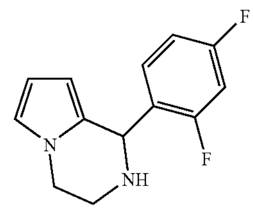 | A |
| AM9 | 1-(2-fluorophenyl)-1,2,3,4-tetrahydropyrrolo[1,2-a]pyrazine | 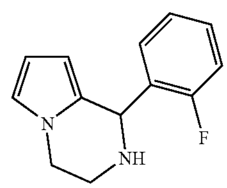 | A |
| AM10 | 1-(3,4-dichlorophenyl)-1,2,3,4-tetrahydropyrrolo[1,2-a]pyrazine | 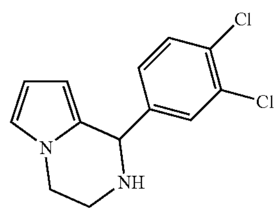 | A |
| AM11 | 1-o-tolyl-1,2,3,4-tetrahydropyrrolo[1,2-a]pyrazine | 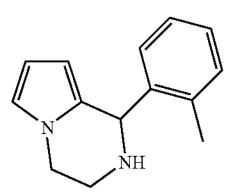 | A |
| AM12 | 1-(2-methoxyphenyl)-1,2,3,4-tetrahydropyrrolo[1,2-a]pyrazine | 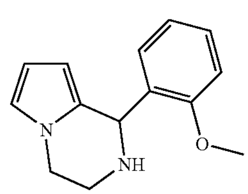 | A |
| AM13 | 1-m-tolyl-1,2,3,4-tetrahydropyrrolo[1,2-a]pyrazine | 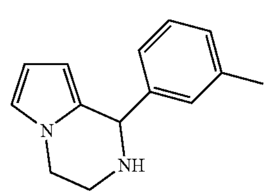 | A |
| AM14 | 1-(2,3-dihydrobenzo[b][1,4]dioxin-6-yl)-1,2,3,4-tetrahydropyrrolo[1,2-a]pyrazine | 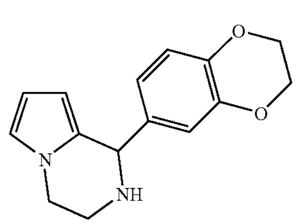 | A |

-continued

| No. | Name | Structure | Method |
|---|---|---|---|
| AM15 | 1-(3-chlorophenyl)-1,2,3,4-tetrahydropyrrolo[1,2-a]pyrazine | 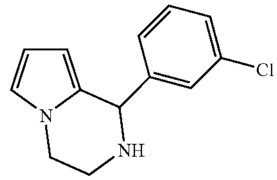 | A |
| AM16 | N,N-dimethyl-4-(1,2,3,4-tetrahydropyrrolo[1,2-a]pyrazin-1-yl)aniline | 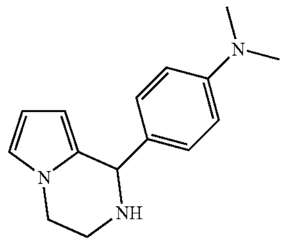 | A |
| AM17 | 1-methyl-1,2,3,4-tetrahydropyrrolo[1,2-a]pyrazine | 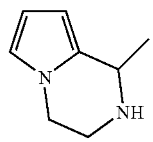 | B |

The following acid units were used for synthesis of the example compounds. All the acids and acid chlorides used are commercially obtainable.

| No. | Name |
|---|---|
| AC1 | 3-fluorobenzoic acid |
| AC2 | cyclopentylcarboxylic acid |
| AC3 | benzo[d][1,3]dioxol-5-carboxylic acid |
| AC4 | 2-methoxybenzoic acid |
| AC5 | furan-2-carboxylic acid |
| AC6 | cyclopropylcarboxylic acid |
| AC7 | 2-methylbenzoic acid |
| AC8 | 4-fluorobenzoic acid |
| AC9 | thiophene-2-carboxylic acid |
| AC10 | 3-methylbutyric acid |
| AC11 | 2-methoxyacetic acid |
| AC12 | cyclobutylcarboxylic acid |
| AC13 | 2-methylbutyric acid |
| AC14 | 2-fluorobenzoic acid |
| AC15 | 2-methylpropionic acid |
| AC16 | 3-methyl-thiophene-2-carboxylic acid |
| AC17 | 3-(2,4-difluorophenyl)acrylic acid |
| AC18 | cinnamic acid |
| AC19 | 3-(4-fluorophenyl)acrylic acid |
| AC20 | 3-(4-trifluoromethylthio)phenyl)acrylic acid |
| AC21 | 3-phenylpropionic acid |
| AC22 | 5-phenylvaleric acid |
| AC23 | hexanecarboxylic acid |
| AC27 | benzoic acid chloride |
| AC28 | acetic acid chloride |
| AC29 | 2-phenylacetyl chloride |
| AC30 | 3,3-dimethylbutanoyl chloride |
| AC31 | 3-cyclohexalpropanoic acid |
| AC32 | 4-phenylbutyric acid |

Acylation of the 1-aryltetrahydropyrrolopyrazines

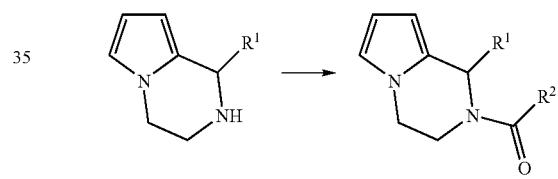

Automated Synthesis

In a reactor (6×8 matrix) with the possibility of heating and stirring, a solution comprising TEA and 1-aryl-tetrahydropyrrolopyrazine (200 µmol) was first initially introduced in a conical screw-cap glass (0.6-2 ml) with the aid of a Cavro RSP 9000 robot system. The solution was prepared by first dissolving 3 mol eq. of TEA in DCE and then adding 1 mol eq. of the 1-aryl-tetrahydropyrrolopyrazine. The solution prepared in this way was then homogenized in an ultrasonic bath and diluted until the concentration of the 1-aryl-tetrahydropyrrolopyrazine was 0.1-0.25 mol/l. 210 µmol of the corresponding acid chloride (0.5 M in DCE, 0.42 ml) were added to this solution and the mixture was stirred at room temperature until the reaction was complete (TLC control). Purification was carried out with the aid of a Cavro RSP 9000 robot system. For purification, $K_2CO_3$ solution (5% in water, 1 ml) was first pipetted in to remove residues of the carboxylic acids. The organic phase was then washed with water (1 ml). If traces of the carboxylic acid were still detected according to the TLC control, tris-(aminoethyl)-amine scavenger resin was used. To separate off any traces of the 1-aryl-tetrahydropyrrolopyrazine present, the organic phase was washed with HCl solution (3% in water, 1 ml) and then with $K_2CO_3$ solution (5% in water, 1 ml). The organic phase was diluted with ethanol (0.5 ml) and transferred into tared glasses. The solvent was then stripped off to constant weight in vacuo.

The following compounds were prepared by this method.

| No. | Name | M+ |
|---|---|---|
| 1 | (3-fluorophenyl)(1-(2-methoxyphenyl)-3,4-dihydropyrrolo[1,2-a]pyrazin-2(1H)-yl)methanone | 350.1 |
| 2 | cyclopentyl-[1-(2-methoxy-phenyl)-3,4-dihydro-1H-pyrrolo[1,2-a]pyrazin-2-yl]-methanone | 324.2 |
| 3 | benzo[1,3]dioxol-5-yl-[1-(2-methoxy-phenyl)-3,4-dihydro-1H-pyrrolo[1,2-a]pyrazin-2-yl]-methanone | 376.1 |
| 4 | (2-methoxy-phenyl)-[1-(2-methoxy-phenyl)-3,4-dihydro-1H-pyrrolo[1,2-a]pyrazin-2-yl]-methanone | 362.2 |
| 5 | (1-(2-fluorophenyl)-3,4-dihydropyrrolo[1,2-a]pyrazin-2(1H)-yl)(furan-2-yl)methanone | 310.1 |
| 6 | cyclopropyl(1-(2-fluorophenyl)-3,4-dihydropyrrolo[1,2-a]pyrazin-2(1H)-yl)methanone | 284.1 |
| 7 | (3-fluoro-phenyl)-[1-(2-fluoro-phenyl)-3,4-dihydro-1H-pyrrolo[1,2-a]pyrazin-2-yl]-methanone | 338.1 |
| 8 | (1-(2-fluorophenyl)-3,4-dihydropyrrolo[1,2-a]pyrazin-2(1H)-yl)(o-tolyl)methanone | 334.1 |
| 9 | benzo[d][1,3]dioxol-5-yl(1-(2-fluorophenyl)-3,4-dihydropyrrolo[1,2-a]pyrazin-2(1H)-yl)methanone | 364.1 |
| 10 | cyclopentyl-(1-o-tolyl-3,4-dihydro-1H-pyrrolo[1,2-a]pyrazin-2-yl)-methanone | 308.2 |
| 11 | o-tolyl(1-o-tolyl-3,4-dihydropyrrolo[1,2-a]pyrazin-2(1H)-yl)methanone | 330.2 |
| 12 | benzo[d][1,3]dioxol-5-yl(1-o-tolyl-3,4-dihydropyrrolo[1,2-a]pyrazin-2(1H)-yl)methanone | 360.1 |
| 13 | (4-fluoro-phenyl)-(1-m-tolyl-3,4-dihydro-1H-pyrrolo[1,2-a]pyrazin-2-yl)-methanone | 334.1 |
| 14 | thiophen-2-yl(1-m-tolyl-3,4-dihydropyrrolo[1,2-a]pyrazin-2(1H)-yl)methanone | 322.1 |
| 15 | 3-methyl-1-(1-m-tolyl-3,4-dihydropyrrolo[1,2-a]pyrazin-2(1H)-yl)butan-1-one | 296.2 |
| 16 | (3-fluoro-phenyl)-(1-m-tolyl-3,4-dihydro-1H-pyrrolo[1,2-a]pyrazin-2-yl)-methanone | 334.1 |
| 17 | cyclopentyl(1-m-tolyl-3,4-dihydropyrrolo[1,2-a]pyrazin-2(1H)-yl)methanone | 308.2 |
| 18 | benzo[1,3]dioxol-5-yl-(1-m-tolyl-3,4-dihydro-1H-pyrrolo[1,2-a]pyrazin-2-yl)-methanone | 360.1 |
| 19 | (1-(2,4-difluorophenyl)-3,4-dihydropyrrolo[1,2-a]pyrazin-2(1H)-yl)(4-fluorophenyl)methanone | 356.1 |
| 20 | (4-fluorophenyl)(1-phenyl-3,4-dihydropyrrolo[1,2-a]pyrazin-2(1H)-yl)methanone | 320.1 |
| 21 | furan-2-yl(1-phenyl-3,4-dihydropyrrolo[1,2-a]pyrazin-2(1H)-yl)methanone | 292.1 |
| 22 | (1-phenyl-3,4-dihydropyrrolo[1,2-a]pyrazin-2(1H)-yl)(thiophen-2-yl)methanone | 308.1 |
| 23 | (3-fluorophenyl)(1-phenyl-3,4-dihydropyrrolo[1,2-a]pyrazin-2(1H)-yl)methanone | 320.1 |
| 24 | cyclopentyl(1-phenyl-3,4-dihydropyrrolo[1,2-a]pyrazin-2(1H)-yl)methanone | 294.2 |
| 25 | 2-methoxy-1-(1-phenyl-3,4-dihydropyrrolo[1,2-a]pyrazin-2(1H)-yl)ethanone | 270.1 |
| 26 | (1-phenyl-3,4-dihydropyrrolo[1,2-a]pyrazin-2(1H)-yl)(o-tolyl)methanone | 316.2 |
| 27 | (2-methoxyphenyl)(1-phenyl-3,4-dihydropyrrolo[1,2-a]pyrazin-2(1H)-yl)methanone | 332.2 |
| 28 | cyclobutyl(1-(4-fluorophenyl)-3,4-dihydropyrrolo[1,2-a]pyrazin-2(1H)-yl)methanone | 298.1 |
| 29 | (1-(4-chlorophenyl)-3,4-dihydropyrrolo[1,2-a]pyrazin-2(1H)-yl)(2-methoxyphenyl)methanone | 366.1 |
| 30 | furan-2-yl(1-(3-methoxyphenyl)-3,4-dihydropyrrolo[1,2-a]pyrazin-2(1H)-yl)methanone | 322.1 |
| 31 | 2-methyl-1-(1-o-tolyl-3,4-dihydropyrrolo[1,2-a]pyrazin-2(1H)-yl)butan-1-one | 296.2 |
| 32 | (2-fluorophenyl)(1-o-tolyl-3,4-dihydropyrrolo[1,2-a]pyrazin-2(1H)-yl)methanone | 334.1 |
| 33 | benzo[1,3]dioxol-5-yl-[1-(2,3-dihydro-benzo[1,4]dioxin-6-yl)-3,4-dihydro-1H-pyrrolo[1,2-a]pyrazin-2-yl]-methanone | 404.1 |
| 34 | [1-(2,3-dihydro-benzo[1,4]dioxin-6-yl)-3,4-dihydro-1H-pyrrolo[1,2-a]pyrazin-2-yl]-o-tolyl-methanone | 374.2 |
| 35 | [1-(2,3-dihydro-benzo[1,4]dioxin-6-yl)-3,4-dihydro-1H-pyrrolo[1,2-a]pyrazin-2-yl]-(2-fluoro-phenyl)-methanone | 378.1 |
| 36 | [1-(2,3-dihydro-benzo[1,4]dioxin-6-yl)-3,4-dihydro-1H-pyrrolo[1,2-a]pyrazin-2-yl]-thiophen-2-yl-methanone | 366.1 |
| 37 | [1-(2,3-dihydro-benzo[1,4]dioxin-6-yl)-3,4-dihydro-1H-pyrrolo[1,2-a]pyrazin-2-yl]-furan-2-yl-methanone | 350.1 |
| 38 | [1-(2,3-dihydro-benzo[1,4]dioxin-6-yl)-3,4-dihydro-1H-pyrrolo[1,2-a]pyrazin-2-yl]-(4-fluoro-phenyl)-methanone | 378.1 |
| 39 | (1-(3-chlorophenyl)-3,4-dihydropyrrolo[1,2-a]pyrazin-2-(1H)-yl)(2-methoxyphenyl)methanone | 366.1 |
| 40 | benzo[d][1,3]dioxol-5-yl(1-(3-chlorophenyl)-3,4-dihydropyrrolo[1,2-a]pyrazin-2(1H)-yl)methanone | 380.1 |
| 41 | (1-(3-chlorophenyl)-3,4-dihydropyrrolo[1,2-a]pyrazin-2(1H)-yl)(o-tolyl)methanone | 350.1 |
| 42 | (1-(3-chlorophenyl)-3,4-dihydropyrrolo[1,2-a]pyrazin-2(1H)-yl)(cyclopentyl)methanone | 328.1 |
| 43 | [1-(3-chloro-phenyl)-3,4-dihydro-1H-pyrrolo[1,2-a]pyrazin-2-yl]-(3-fluoro-phenyl)-methanone | 354.1 |
| 44 | [1-(3-chloro-phenyl)-3,4-dihydro-1H-pyrrolo[1,2-a]pyrazin-2-yl]-(2-fluoro-phenyl)-methanone | 354.1 |
| 45 | [1-(3-chloro-phenyl)-3,4-dihydro-1H-pyrrolo[1,2-a]pyrazin-2-yl]-thiophen-2-yl-methanone | 342.1 |
| 46 | [1-(3-chloro-phenyl)-3,4-dihydro-1H-pyrrolo[1,2-a]pyrazin-2-yl]-(4-fluoro-phenyl)-methanone | 354.1 |
| 47 | (2-fluorophenyl)(1-(2-fluorophenyl)-3,4-dihydropyrrolo[1,2-a]pyrazin-2(1H)-yl)methanone | 338.1 |
| 48 | 1-(1-(2-methoxyphenyl)-3,4-dihydropyrrolo[1,2-a]pyrazin-2(1H)-yl)-2-methylbutan-1-one | 312.2 |
| 49 | (2-fluorophenyl)(1-(2-methoxyphenyl)-3,4-dihydropyrrolo[1,2-a]pyrazin-2(1H)-yl)methanone | 350.1 |
| 50 | (1-(4-(dimethylamino)phenyl)-3,4-dihydropyrrolo[1,2-a]pyrazin-2(1H)-yl)(o-tolyl)methanone | 359.2 |
| 51 | (1-(4-(dimethylamino)phenyl)-3,4-dihydropyrrolo[1,2-a]pyrazin-2(1H)-yl)(2-fluorophenyl)methanone | 363.2 |
| 52 | cyclopropyl(1-(4-(dimethylamino)phenyl)-3,4-dihydropyrrolo[1,2-a]pyrazin-2(1H)-yl)methanone | 309.2 |
| 53 | (1-(4-(dimethylamino)phenyl)-3,4-dihydropyrrolo[1,2-a]pyrazin-2(1H)-yl)(thiophen-2-yl)methanone | 351.1 |
| 54 | (1-(4-(dimethylamino)phenyl)-3,4-dihydropyrrolo[1,2-a]pyrazin-2(1H)-yl)(4-fluorophenyl)methanone | 363.2 |
| 55 | 2-methoxy-1-(1-(thiophen-2-yl)-3,4-dihydropyrrolo[1,2-a]pyrazin-2(1H)-yl)butan-1-one | 288.1 |
| 56 | benzo[1,3]dioxol-5-yl-(1-thiophen-2-yl-3,4-dihydro-1H-pyrrolo[1,2-a]pyrazin-2-yl)-methanone | 352.1 |
| 57 | (1-(thiophen-2-yl)-3,4-dihydropyrrolo[1,2-a]pyrazin-2(1H)-yl)(o-tolyl)methanone | 322.1 |
| 58 | (3-fluoro-phenyl)-(1-thiophen-2-yl-3,4-dihydro-1H-pyrrolo[1,2-a]pyrazin-2-yl)-methanone | 326.1 |
| 59 | cyclopropyl(1-(thiophen-2-yl)-3,4-dihydropyrrolo[1,2-a]pyrazin-2(1H)-yl)methanone | 272.1 |
| 60 | (4-fluorophenyl)(1-(thiophen-2-yl)-3,4-dihydropyrrolo[1,2-a]pyrazin-2(1H)-yl)methanone | 326.1 |
| 61 | benzo[1,3]dioxol-5-yl-[1-(3,4-dichloro-phenyl)-3,4-dihydro-1H-pyrrolo[1,2-a]pyrazin-2-yl]-methanone | 414.1 |
| 62 | cyclopentyl-[1-(3,4-dichloro-phenyl)-3,4-dihydro-1H-pyrrolo[1,2-a]pyrazin-2-yl]-methanone | 362.1 |
| 63 | [1-(3,4-dichloro-phenyl)-3,4-dihydro-1H-pyrrolo[1,2-a]pyrazin-2-yl]-(2-fluoro-phenyl)-methanone | 388.1 |
| 64 | 1-(1-(3,4-dichlorophenyl)-3,4-dihydropyrrolo[1,2-a]pyrazin-2(1H)-yl)-3-methylbutan-1-one | 350.1 |
| 65 | (1-(3,4-Dichlorophenyl)-3,4-dihydropyrrolo[1,2-a]pyrazin-2(1H)-yl)(thiophen-2-yl)methanone | 376.0 |
| 66 | cyclobutyl(1-(3,4-dichlorophenyl)-3,4-dihydropyrrolo[1,2-a]pyrazin-2(1H)-yl)methanone | 348.1 |
| 67 | 1-(1-(3,4-dichlorophenyl)-3,4-dihydropyrrolo[1,2-a]pyrazin-2(1H)-yl)-2-methylpropan-1-one | 336.1 |
| 68 | [1-(3,4-dichloro-phenyl)-3,4-dihydro-1H-pyrrolo[1,2-a]pyrazin-2-yl]-furan-2-yl-methanone | 360.0 |
| 69 | (2-fluorophenyl)(1-p-tolyl-3,4-dihydropyrrolo[1,2-a]pyrazin-2(1H)-yl)methanone | 334.1 |

Synthesis of Example Compounds 70, 71 and 87

The corresponding carboxylic acid (1.5 mmol), EDCI (0.29 g, 1.5 mmol), HOBt (0.15 g, 1.1 mmol) and diisopropylethylamine (0.25 g, 2.5 mmol) were added in succession to a solution of the amine (0.2 g, 1 mmol) in MC (20 ml) and the mixture was stirred at room temperature for 16 hours. When the reaction had ended, sodium bicarbonate solution was added, the phases were separated and the aqueous phase was extracted once more with MC. The combined organic phases were dried over magnesium sulfate and concentrated. Purification was carried out by column chromatography on silica gel (mobile phase: MC→MC/methanol 99:1)

Synthesis of Example Compounds 72 and 74

The corresponding cinnamic acid (1 eq.) and the corresponding amine (AM3 or AM7) were dissolved in THF, and HATU (eq.) and TEA (2 eq.) were added. The mixture was stirred at room temperature overnight. The sample was washed several times with saturated NaCl solution and evaporated to dryness and the residue was purified by column chromatography.

Example 72: Mobile phase: ethyl acetate/cyclohexane, 1:2

Example 74: Mobile phase: ethyl acetate/cyclohexane, 1:5

Synthesis of Example Compounds 73

The amine AM17 (1 eq.) was initially introduced into the flask together with the corresponding acid (1 eq.) under nitrogen. TBTU (1 eq.) and HOBT (1 eq.) were then added and the solids were dissolved in THF (8.5 ml/mmol of amine). N-ethyldiisopropylamine (2 eq.) was added to this mixture with constant stirring and the mixture was subsequently stirred at room temperature overnight. Ethyl acetate was added to the reaction solution and the mixture was washed with sat. NaCl solution, NaHCO$_3$ solution, NaCl and with NH$_4$HSO$_3$ solution and evaporated to dryness with nitrogen and the residue was dried overnight using an oil pump. It was possible to obtain the desired product by means of flash column chromatography (mobile phase: ethyl acetate/cyclohexane, 1:5).

Synthesis of Example Compounds 75, 76, 78 and 82-85

The corresponding amine (1.0 mmol) was dissolved in MC (10 ml), and triethylamine (279 µl, 2.0 mmol) and the corresponding acid chloride (1.1 mmol) were added in succession. The reaction mixture was stirred at room temperature for 2 hours (TLC control). When the reaction had ended, the mixture was diluted with MC (20 ml), washed with water and dried over magnesium sulfate. The solvent was then removed completely and the crude product was purified by column chromatography on silica gel (mobile phase: hexane/ethyl acetate, 3:2).

Synthesis of Example Compound 77 and 86

The corresponding amine (1.0 mmol) was dissolved in MC (50 ml), and first the corresponding acid chloride (1.5 mmol) and then PS-DCC resin (1.6 g, 2 mmol) were added. The reaction mixture was shaken at room temperature overnight. When the reaction had ended (TLC control), the resin was filtered off and washed successively with MC and methanol. The combined organic phase was concentrated and the crude product was purified by column chromatography on silica gel (mobile phase: hexane/ethyl acetate, 3:2).

| | Structure | [M+] m/z | Yield |
|---|---|---|---|
| 70 | (3-methylthiophen-2-yl)(1-phenyl-3,4-dihydropyrrolo[1,2-a]pyrazin-2(1H)-yl)methanone | 322.1 | 67% |
| 71 | 3-(2,4-difluorophenyl)-1-(1-phenyl-3,4-dihydropyrrolo[1,2-a]pyrazin-2(1H)-yl)prop-2-en-1-one | 364.1 | 65% |
| 72 | 3-phenyl-1-(1-(thiophen-2-yl)-3,4-dihydropyrrolo[1,2-a]pyrazin-2(1H)-yl)prop-2-en-1-one | 334.0 | 61% |
| 73 | 3-(4-fluorophenyl)-1-(1-methyl-3,4-dihydropyrrolo[1,2-a]pyrazin-2(1H)-yl)prop-2-en-1-one | 284.0 | 49% |
| 74 | 1-(1-methyl-3,4-dihydropyrrolo[1,2-a]pyrazin-2(1H)-yl)-3-(4-(trifluoromethylthio)phenyl)prop-2-en-1-one | 366.0 | 52% |

-continued

| | Structure | [M+] m/z | Yield |
|---|---|---|---|
| 75 | (1-(4-fluorophenyl)-3,4-dihydropyrrolo[1,2-a]pyrazin-2(1H)-yl)(o-tolyl)methanone | 334.1 | |
| 76 | 3-phenyl-1-(1-(thiophen-2-yl)-3,4-dihydropyrrolo[1,2-a]pyrazin-2(1H)-yl)propan-1-one | 336.1 | |
| 77 | 5-phenyl-1-(1-(thiophen-2-yl)-3,4-dihydropyrrolo[1,2-a]pyrazin-2(1H)-yl)pentan-1-one | 364.2 | |
| 78 | 1-(1-(thiophen-2-yl)-3,4-dihydropyrrolo[1,2-a]pyrazin-2(1H)-yl)hexan-1-one | 302.1 | |
| 82 | phenyl(1-(thiophen-2-yl)-3,4-dihydropyrrolo[1,2-a]pyrazin-2(1H)-yl)methanone | 308.1 | 68 |
| 83 | 1-(1-(thiophen-2-yl)-3,4-dihydropyrrolo[1,2-a]pyrazin-2(1H)-yl)ethanone | 246.1 | 69 |
| 84 | 2-phenyl-1-(1-(thiophen-2-yl)-3,4-dihydropyrrolo[1,2-a]pyrazin-2(1H)-yl)ethanone | 322.1 | 49 |
| 85 | 3,3-dimethyl-1-(1-(thiophen-2-yl)-3,4-dihydropyrrolo[1,2-a]pyrazin-2(1H)-yl)butan-1-one | 302.1 | 27 |
| 86 | 3-cyclohexyl-1-(1-(thiophen-2-yl)-3,4-dihydropyrrolo[1,2-a]pyrazin-2(1H)-yl)propan-1-one | 342.2 | 84 |
| 87 | 4-phenyl-1-(1-(thiophen-2-yl)-3,4-dihydropyrrolo[1,2-a]pyrazin-2(1H)-yl)butan-1-one | 350.1 | 27 |

Biological Data

Inhibition of NA and 5HT Uptake

In order to be able to carry out these in vitro studies, synaptosomes are freshly isolated from areas of the rat brain. In each case a so-called "$P_2$" fraction prepared in accordance with the instructions of Gray and Whittaker (E. G. Gray and V. P. Whittaker (1962) J. Anat. 76, 79-88) is prepared. For the NA uptake, these vesicular particles are isolated from the hypothalamus of male rat brains. A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

| No. | Serotonin reuptake % inhibition [10 μmol] | NA reuptake % inhibition [10 μmol] |
|---|---|---|
| 1 | 26 | — |
| 2 | 79 | 36 |
| 3 | 86 | 29 |
| 4 | 82 | 13 |
| 5 | 11 | 34 |
| 6 | 34 | 13 |
| 7 | 54 | 36 |
| 8 | 37 | 18 |
| 9 | 30 | 27 |
| 10 | 50 | 30 |
| 11 | 38 | — |
| 12 | 34 | 22 |
| 13 | 55 | 41 |
| 14 | 27 | 25 |
| 15 | 28 | 19 |
| 16 | 54 | 49 |
| 17 | 34 | 21 |
| 18 | 55 | 40 |
| 19 | 35 | 28 |
| 20 | 32 | 33 |
| 21 | 11 | 44 |
| 22 | 18 | 33 |
| 23 | 42 | 41 |
| 24 | 32 | 44 |
| 25 | 33 | 12 |
| 26 | 32 | 23 |
| 27 | 28 | 15 |
| 28 | 29 | 21 |
| 29 | 34 | 21 |
| 30 | 51 | 16 |
| 31 | 26 | — |
| 32 | 29 | 14 |
| 33 | 52 | 26 |
| 34 | 52 | 22 |
| 35 | 66 | 43 |
| 36 | 59 | 41 |
| 37 | 55 | 32 |
| 38 | 58 | 48 |
| 39 | 46 | 43 |
| 40 | 38 | 41 |
| 41 | 37 | 35 |
| 42 | 30 | 22 |
| 43 | 58 | 66 |
| 44 | 53 | 41 |
| 45 | 53 | 43 |
| 46 | 52 | 50 |
| 47 | 18 | 12 |
| 48 | 27 | — |
| 49 | 47 | 12 |
| 50 | 41 | 14 |
| 51 | 43 | 19 |
| 52 | 27 | 16 |
| 53 | 31 | 26 |
| 54 | 47 | 40 |
| 55 | 28 | — |
| 56 | 56 | 35 |
| 57 | 44 | 15 |
| 58 | 60 | 54 |
| 59 | 31 | 10 |
| 60 | 37 | 11 |
| 61 | 64 | 68 |
| 62 | 51 | 29 |
| 63 | 65 | 71 |
| 64 | 48 | 30 |
| 65 | 43 | 49 |
| 66 | 43 | 32 |
| 67 | 46 | 46 |
| 68 | 57 | 48 |
| 69 | 40 | 12 |
| 70 | 38 | 11 |
| 71 | 27 | 17 |
| 72 | 28 | 23 |
| 73 | 25 | — |
| 74 | 32 | — |
| 75 | 38 | 17 |
| 76 | 36 | 46 |
| 77 | 25 | 10 |
| 78 | 51 | — |
| 82 | — | 35 |
| 83 | 16 | — |
| 84 | — | — |
| 85 | 12 | — |
| 86 | 53 | 19 |
| 87 | 17 | — |

LIST OF ABBREVIATIONS eq. equivalent
TLC thin layer chromatography
DCE 1,2-dichloroethane
MC methylene chloride
EDCI N-(3-dimethylaminopropyl)-N'-ethyl-carbodiimide
h hours(s)
HOBt 1-hydroxy-1H-benzotriazole
m/z mass to charge ratio
TEA triethylamine
HATU O-(7-azabenzotriazol-1-yl)-N,N,N',N'-tetramethyluronium hexafluorophosphate
CDI 1,1'-carbonyl diimidazole
sat. saturated The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:
1. A compound selected from the group consisting of:
(3-fluorophenyl)(1-(2-methoxyphenyl)-3,4-dihydropyrrolo[1,2-a]pyrazin-2(1H)-yl)methanone;
cyclopentyl-[1-(2-methoxy-phenyl)-3,4-dihydro-1H-pyrrolo[1,2-a]pyrazin-2-yl]-methanone;
benzo[1,3]dioxol-5-yl-[1-(2-methoxy-phenyl)-3,4-dihydro-1H-pyrrolo[1,2-a]pyrazin-2-yl]-methanone;
(2-methoxy-phenyl)-[1-(2-methoxy-phenyl)-3,4-dihydro-1H-pyrrolo[1,2-a]pyrazin-2-yl]-methanone;
(1-(2-fluorophenyl)-3,4-dihydropyrrolo[1,2-a]pyrazin-2(1H)-yl)(furan-2-yl)methanone;
cyclopropyl(1-(2-fluorophenyl)-3,4-dihydropyrrolo[1,2-a]pyrazin-2(1H)-yl)methanone;
(3-fluoro-phenyl)-[1-(2-fluoro-phenyl)-3,4-dihydro-1H-pyrrolo[1,2-a]pyrazin-2-yl]-methanone;
(1-(2-fluorophenyl)-3,4-dihydropyrrolo[1,2-a]pyrazin-2(1H)-yl)(o-tolyl)methanone;
benzo[d][1,3]dioxol-5-yl(1-(2-fluorophenyl)-3,4-dihydropyrrolo[1,2-a]pyrazin-2(1H)-yl)methanone;
cyclopentyl-(1-o-tolyl-3,4-dihydro-1H-pyrrolo[1,2-a]pyrazin-2-yl)-methanone;

o-tolyl(1-o-tolyl-3,4-dihydropyrrolo[1,2-a]pyrazin-2 (1H)-yl)methanone;
benzo[d][1,3]dioxol-5-yl(1-o-tolyl-3,4-dihydropyrrolo[1, 2-a]pyrazin-2(1H)-yl)methanone;
(4-fluoro-phenyl)-(1-m-tolyl-3,4-dihydro-1H-pyrrolo[1, 2-a]pyrazin-2-yl)-methanone;
Thiophen-2-yl(1-m-tolyl-3,4-dihydropyrrolo[1,2-a] pyrazin-2(1H)-yl)methanone;
(3-fluoro-phenyl)-(1-m-tolyl-3,4-dihydro-1H-pyrrolo[1, 2-a]pyrazin-2-yl)-methanone;
cyclopentyl(1-m-tolyl-3,4-dihydropyrrolo[1,2-a]pyrazin- 2(1H)-yl)methanone;
benzo[1,3]dioxol-5-yl-(1-m-tolyl-3,4-dihydro-1H-pyrrolo[1,2-a]pyrazin-2-yl)-methanone;
(1-(2,4-difluorophenyl)-3,4-dihydropyrrolo[1,2-a] pyrazin-2(1H)-yl)(4-fluorophenyl)methanone;
(4-fluorophenyl)(1-phenyl-3,4-dihydropyrrolo[1,2-a] pyrazin-2(1H)-yl)methanone;
(1-phenyl-3,4-dihydropyrrolo[1,2-a]pyrazin-2(1H)-yl) (thiophen-2-yl)methanone;
(3-fluorophenyl)(1-phenyl-3,4-dihydropyrrolo[1,2-a] pyrazin-2(1H)-yl)methanone;
cyclopentyl(1-phenyl-3,4-dihydropyrrolo[1,2-a]pyrazin-2 (1H)-yl)methanone;
2-methoxy-1-(1-phenyl-3,4-dihydropyrrolo[1,2-a] pyrazin-2(1H)-yl)ethanone;
(1-phenyl-3,4-dihydropyrrolo[1,2-a]pyrazin-2(1H)-yl)(o-tolyl)methanone;
(2-methoxyphenyl)(1-phenyl-3,4-dihydropyrrolo[1,2-a] pyrazin-2(1H)-yl)-methanone;
cyclobutyl(1-(4-fluorophenyl)-3,4-dihydropyrrolo[1,2-a] pyrazin-2(1H)-yl)-methanone;
(1-(4-chlorophenyl)-3,4-dihydropyrrolo[1,2-a]pyrazin-2 (1H)-yl)(2-methoxyphenyl)-methanone;
furan-2-yl(1-(3-methoxyphenyl)-3,4-dihydropyrrolo[1,2-a]pyrazin-2(1H)-yl)methanone;
(2-fluorophenyl)(1-o-tolyl-3,4-dihydropyrrolo[1,2-a] pyrazin-2(1H)-yl)methanone;
benzo[1,3]dioxol-5-yl-[1-(2,3-dihydro-benzo[1,4]dioxin-6-yl)-3,4-dihydro-1H-pyrrolo[1,2-a]pyrazin-2-yl]-methanone;
[1-(2,3-dihydro-benzo[1,4]dioxin-6-yl)-3,4-dihydro-1H-pyrrolo[1,2-a]pyrazin-2-yl]-o-tolyl-methanone;
[1-(2,3-dihydro-benzo[1,4]dioxin-6-yl)-3,4-dihydro-1H-pyrrolo[1,2-a]pyrazin-2-yl]-(2-fluoro-phenyl)-methanone;
[1-(2,3-dihydro-benzo[1,4]dioxin-6-yl)-3,4-dihydro-1H-pyrrolo[1,2-a]pyrazin-2-yl]-thiophen-2-yl-methanone;
[1-(2,3-dihydro-benzo[1,4]dioxin-6-yl)-3,4-dihydro-1H-pyrrolo[1,2-a]pyrazin-2-yl]-furan-2-yl-methanone;
[1-(2,3-dihydro-benzo[1,4]dioxin-6-yl)-3,4-dihydro-1H-pyrrolo[1,2-a]pyrazin-2-yl]-(4-fluoro-phenyl)-methanone;
(1-(3-chlorophenyl)-3,4-dihydropyrrolo[1,2-a]pyrazin-2 (1H)-yl)(2-methoxyphenyl)methanone,
benzo[d][1,3]dioxol-5-yl(1-(3-chlorophenyl)-3,4-dihydropyrrolo[1,2-a]pyrazin-2(1H)-yl)methanone;
(1-(3-chlorophenyl)-3,4-dihydropyrrolo[1,2-a]pyrazin-2 (1H)-yl)(o-tolyl)-methanone;
(1-(3-chlorophenyl)-3,4-dihydropyrrolo[1,2-a]pyrazin-2 (1H)yl)(cyclopentyl)-methanone;
[1-(3-chloro-phenyl)-3,4-dihydro-1H-pyrrolo[1,2-a] pyrazin-2-yl]-(3-fluoro-phenyl)-methanone;
[1-(3-chloro-phenyl)-3,4-dihydro-1H-pyrrolo[1,2-a] pyrazin-2-yl]-(2-fluoro-phenyl)-methanone
[1-(3-chloro-phenyl)-3,4-dihydro-1H-pyrrolo[1,2-a] pyrazin-2-yl]-thiophen-2-yl-methanone;
[1-(3-chloro-phenyl)-3,4-dihydro-1H-pyrrolo[1,2-a] pyrazin-2-yl]-(4-fluoro-phenyl)-methanone;
(2-fluorophenyl)(1-(2-fluorophenyl)-3,4-dihydropyrrolo [1,2-a]pyrazin-2(1H)-yl)-methanone;
(2-fluorophenyl)(1-(2-methoxyphenyl)-3,4-dihydropyrrolo[1,2-a]pyrazin-2(1H)-yl)-methanone;
(1-(4-(dimethylamino)phenyl)-3,4-dihydropyrrolo[1,2-a] pyrazin-2(1H)-yl)(o-tolyl)-methanone;
(1-(4-(dimethylamino)phenyl)-3,4-dihydropyrrolo[1,2-a] pyrazin-2(1H)-yl)(2-fluorophenyl)methanone;
cyclopropyl(1-(4-(dimethylamino)phenyl)-3,4-dihydro-pyrrolo[1,2-a]pyrazin-2(1H)-yl)methanone;
(1-(4-(dimethylamino)phenyl)-3,4-dihydropyrrolo[1,2-a] pyrazin-2(1H)-yl)-(thiophen-2-yl)-methanone;
(1-(4-(dimethylamino)phenyl)-3,4-dihydropyrrolo[1,2-a] pyrazin-2(1H)-yl)(4-fluorophenyl)methanone;
2-methoxy-1-(1-(thiophen-2-yl)-3,4-dihydropyrrolo[1,2-a]pyrazin-2(1H)-yl)butan-1-one;
benzo[1,3]dioxol-5-yl-(1-thiophen-2-yl-3,4-dihydro-1H-pyrrolo[1,2-a]pyrazin-2-yl)-methanone;
(1-(thiophen-2-yl)-3,4-dihydropyrrolo[1,2-a]pyrazin-2 (1H)yl)(o-tolyl)methanone
(3-fluoro-phenyl)-(1-thiophen-2-yl-3,4-dihydro-1H-pyrrolo[1,2-a]pyrazin-2-yl)-methanone;
cyclopropyl(1-(thiophen-2-yl)-3,4-dihydropyrrolo[1,2-a] pyrazin-2(1H)-yl)-methanone;
(4-fluorophenyl)(1-(thiophen-2-yl)-3,4-dihydropyrrolo[1, 2-a]pyrazin-2(1H)-yl)-methanone;
benzo[1,3]dioxol-5-yl-4[-(3,4-dichloro-phenyl)-3,4-dihydro-1H-pyrrolo[1,2-a]pyrazin-2-yl]-methanone;
cyclopentyl-[1-(3,4-dichloro-phenyl)-3,4-dihydro-1H-pyrrolo[1,2-a]pyrazin-2-yl]-methanone;
[1-(3,4-dichloro-phenyl)-3,4-dihydro-1H-pyrrolo[1,2-a] pyrazin-2-yl]-(2-fluoro-phenyl)-methanone;
1-(1-(3,4-dichlorophenyl)-3,4-dihydropyrrolo[1,2-a] pyrazin-2(1H)-yl)-3-methylbutan-1-one;
(1-(3,4-Dichlorophenyl)-3,4-dihydropyrrolo[1,2-a] pyrazin-2(1H)-yl)(thiophen-2-yl)-methanone cyclobutyl(1-(3,4-dichlorophenyl)-3,4-dihydropyrrolo[1,2-a] pyrazin-2(1H)-yl)-methanone
1-(1-(3,4-dichlorophenyl)-3,4-dihydropyrrolo[1,2-a] pyrazin-2(1H)-yl)-2-methylpropan-1-one;
[1-(3,4-dichloro-phenyl)-3,4-dihydro-1H-pyrrolo[1,2-a] pyrazin-2-yl]-furan-2-yl-methanone;
(2-fluorophenyl)(1-p-tolyl-3,4-dihydropyrrolo[1,2-a] pyrazin-2(1H)-yl)methanone;
(3-methylthiophen-2-yl)(1-phenyl-3,4-dihydropyrrolo[1, 2-a]pyrazin-2(1H)-yl)-methanone;
3-(2,4-difluorophenyl)-1-(1-phenyl-3,4-dihydropyrrolo [1,2-a]pyrazin-2(1H)-yl)-prop-2-en-1-one;
3-phenyl-1-(1-(thiophen-2-yl)-3,4-dihydropyrrolo[1,2-a] pyrazin-2(1H)-yl)prop-2-en-1-one;
3-(4-fluorophenyl)-1-(1-methyl-3,4-dihydropyrrolo[1,2-a]pyrazin-2(1H)-yl)prop-2-en-1-one;
1-(1-methyl-3,4-dihydropyrrolo[1,2-a]pyrazin-2(1H)-yl)-3-(4-(trifluoromethylthio)-phenyl)prop-2-en-1-one;
(1-(4-fluorophenyl)-3,4-dihydropyrrolo[1,2-a]pyrazin-2 (1H)-yl)(o-tolyl)methanone;
3-phenyl-1-(1-(thiophen-2-yl)-3,4-dihydropyrrolo[1,2-a] pyrazin-2(1H)-yl)propan-1-one;
5-phenyl-1-(1-(thiophen-2-yl)-3,4-dihydropyrrolo[1,2-a] pyrazin-2(1H)-yl)pentan-1-one;
1-(1-(thiophen-2-yl)-3,4-dihydropyrrolo[1,2-a]pyrazin-2 (1H)-yl)hexan-1-one;
phenyl(1-(thiophen-2-yl)-3,4-dihydropyrrolo[1,2-a] pyrazin-2(1H)-yl)methanone;

1-(1-(thiophen-2-yl)-3,4-dihydropyrrolo[1,2-a]pyrazin-2 (1H)-yl)ethanone;

2-phenyl-1-(1-(thiophen-2-yl)-3,4-dihydropyrrolo[1,2-a] pyrazin-2(1H)-yl)-ethanone;

3,3-dimethyl-1-(1-(thiophen-2-yl)-3,4-dihydropyrrolo[1, 2-a]pyrazin-2(1H)-yl)-butan-1-one;

3-cyclohexyl-1-(1-(thiophen-2-yl)-3,4-dihydropyrrolo[1, 2-a]pyrazin-2(1H)-yl)-propan-1-one, and 4-phenyl-1-(1-(thiophen-2-yl)-3,4-dihydropyrrolo[1,2-a] pyrazin-2(1H)-yl)butan-1-one, and pharmaceutically acceptable salts thereof.

2. A pharmaceutical composition comprising a compound selected from the group consisting of:

3-methyl-1-(1-m-tolyl-3,4-dihydropyrrolo[1,2-a]pyrazin-2(1H)-yl)butan-1-one;

furan-2-yl(1-phenyl-3,4-dihydropyrrolo[1,2-a]pyrazin-2 (1H)-yl)methanone;

2-methyl-1-(1-o-tolyl-3,4-dihydropyrrolo[1,2-a]pyrazin-2(1H)-yl)butan-1-one;

1-(1-(2-methoxyphenyl)-3,4-dihydropyrrolo[1,2-a] pyrazin-2(1H)-yl)-2-methylbutan-1-one, and pharmaceutically acceptable salts thereof.

* * * * *